United States Patent
Ullery

(10) Patent No.: US 10,475,527 B2
(45) Date of Patent: Nov. 12, 2019

(54) METHOD AND SYSTEM FOR DETECTION OF MICROBIAL GROWTH IN A SPECIMEN CONTAINER

(71) Applicant: BIOMERIEUX, INC., Durham, NC (US)

(72) Inventor: Michael Ullery, St. Louis, MO (US)

(73) Assignee: bioMerieux, Inc., Durham, NC (US)

( * ) Notice: Subject to any disclaimer, the term of this patent is extended or adjusted under 35 U.S.C. 154(b) by 114 days.

(21) Appl. No.: 13/788,398

(22) Filed: Mar. 7, 2013

(65) Prior Publication Data

US 2013/0252271 A1     Sep. 26, 2013

Related U.S. Application Data

(60) Provisional application No. 61/614,037, filed on Mar. 22, 2012.

(51) Int. Cl.
| | |
|---|---|
| *G16B 99/00* | (2019.01) |
| *C12Q 1/02* | (2006.01) |
| *C12Q 1/04* | (2006.01) |
| *C12M 1/34* | (2006.01) |

(52) U.S. Cl.
CPC ............. *G16B 99/00* (2019.02); *C12M 1/34* (2013.01); *C12M 41/36* (2013.01); *C12M 41/46* (2013.01); *C12Q 1/02* (2013.01); *C12Q 1/04* (2013.01)

(58) Field of Classification Search
None
See application file for complete search history.

(56) References Cited

U.S. PATENT DOCUMENTS

| | | | | |
|---|---|---|---|---|
| 5,518,895 A | * | 5/1996 | Thorpe et al. | 435/34 |
| 5,856,175 A | * | 1/1999 | Thorpe et al. | 435/287.5 |
| 2002/0086277 A1 | | 7/2002 | Chang et al. | |
| 2010/0092429 A1 | | 4/2010 | Nina et al. | |
| 2011/0029252 A1 | | 2/2011 | Beaty | |

FOREIGN PATENT DOCUMENTS

| | | |
|---|---|---|
| EP | 1804172 A2 | 4/2007 |
| JP | 2010512145 A1 | 4/2010 |
| WO | 2010147621 A1 | 12/2010 |

OTHER PUBLICATIONS

Curran et al. (J Cogn Dev. Author manuscript; available in PMC Jul. 7, 2011; Published in final edited form as: J Cogn Dev. 2010; 11(2): 121-136).*
Haighton (The Nuffield Foundation, posted Oct. 1, 2004).*
Widedel (Grundpraktikum Mikrobiologie 3 Sem, corrected in Jun. 5, 2010).*
Richards (Journ Exp Bot V 10, No. 29 pp. 290-300, Jun. 1959).*
Jaskari, et al., Oat β-glucan and xylan hydrolysates as selective substrates for Bifidobacterium and Lactobacillus strains, Appl Microbial Biotechnol, 1998, 49: 175-181.
Harinen, et al. "Turbidometric Growth Curve Measurements and Liquid Evaporation Studies with a Microplate Photometer", Application Note: AN-MR-MSFC10-0310, Thermo Fisher Scientific, Inc., copyright 2010.
Jorgensen, et al., Microbiological quality and shelf life prediction of chilled fish, Int'l Journal of Food Microbiol, 1988, 295-307, vol. 6.
Kornalijnslijper, et al., Bacterial growth during the early phase of infection determines the severity of experimental *Escherichia coli* mastitis in dairy cows, Veterinary Microbiology, 2004, 177-186, 101.
Lourenco, et al., Antibiotic microbial assay using kinetic-reading microplate system, Brazilian Journal of Pharma. Sciences, Jul./Sep. 2011, 573-584, vol. 47, No. 3.
Vadasz and Vadasz, Predictive modeling of microorganisms: LAG and LIP in monotonic growth, Journal of Food Microbiology, 2005, vol. 102, pp. 257-275.

* cited by examiner

*Primary Examiner* — Joseph Woitach

(57) ABSTRACT

A method for determining whether microbial growth is occurring within a specimen container includes steps of incubating the specimen container and obtaining a series of measurement data points while the specimen container is incubated and storing the data points in a machine-readable memory. The series of measurement data points represent a growth curve of microbial growth within the specimen container. The methods determine a positive condition of microbial growth within the container from the measurement data points.

10 Claims, 22 Drawing Sheets

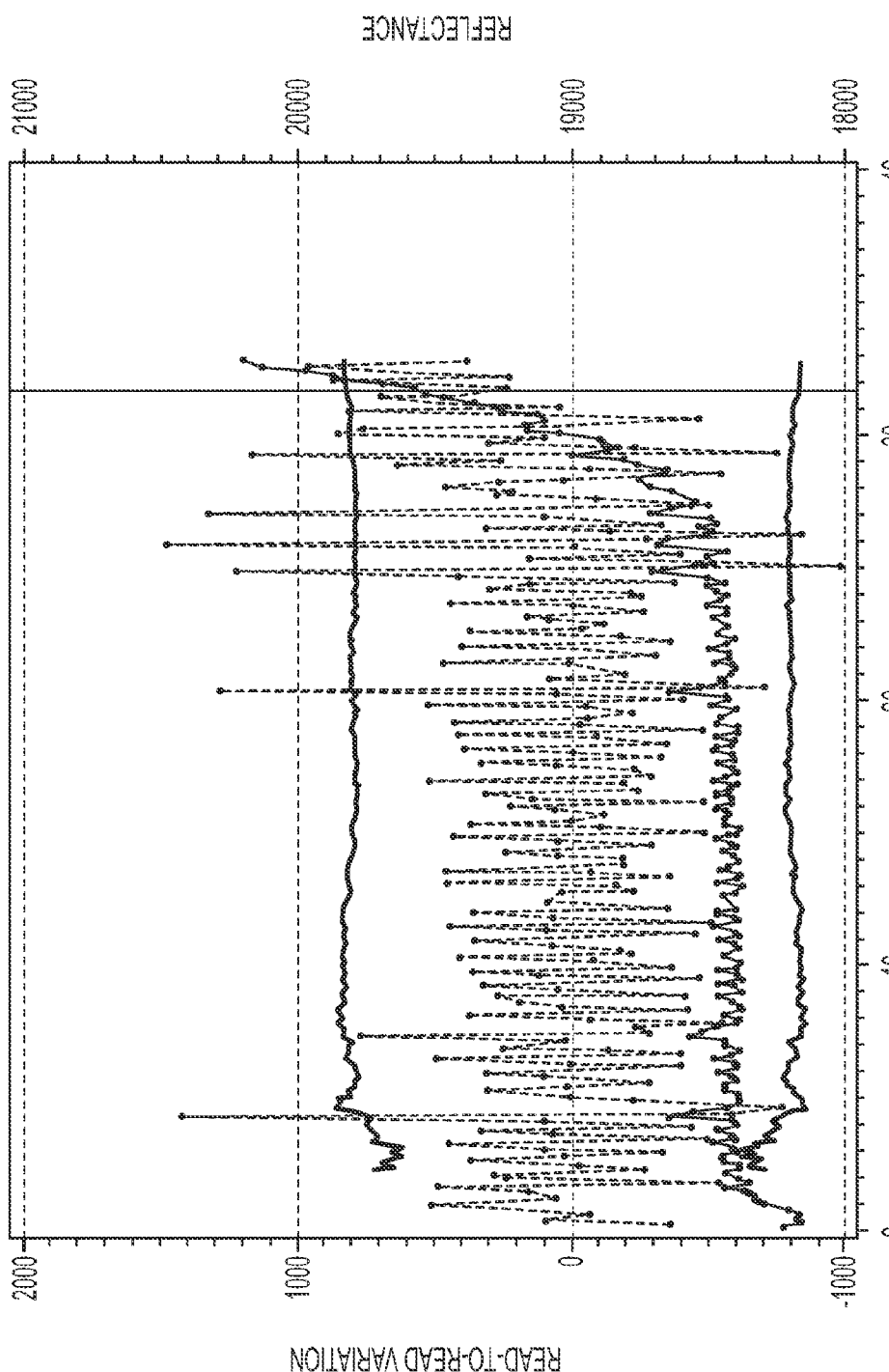

METHOD AND SYSTEM FOR DETECTION OF MICROBIAL GROWTH IN A SPECIMEN CONTAINER

CROSS REFERENCE TO RELATED APPLICATIONS

This application claims priority benefit under 35 U.S.C. § 119(e) to U.S. provisional application Ser. No. 61/614,037 filed Mar. 22, 2012, the entire content of which is incorporated by reference herein.

BACKGROUND

This disclosure relates generally to the field of systems and methods for determining whether an agent (e.g., bacterium) is present in a biological or clinical sample such as blood or urine.

Instruments currently exist on the market in the U.S. that detect the growth and therefore the presence of a microorganism in a blood sample. One such instrument is the BacT/ALERT 3D instrument of the present assignee bioMérieux, Inc. The instrument receives a blood culture bottle containing a blood sample, e.g., from a human patient. The instrument incubates the bottle. Periodically during incubation an optical detection unit in the incubator analyzes a colorimetric sensor incorporated into the bottle. The reflection measurements obtained by the detection unit are used to detect whether microbial growth has occurred within the bottle. The optical detection unit, specimen containers and sensors are described in the patent literature, see U.S. Pat. Nos. 4,945,060; 5,094,955; 5,162,229; 5,164,796; 5,217,876; 5,795,773; and 5,856,175, the entire content of each of which is incorporated by reference herein. U.S. Pat. Nos. 5,856,175 and 5,164,796 describe methods for determining whether microbial growth is occurring with a sample container.

The performance of the positive bottle detection algorithm of the BacT/ALERT instrument is considered commercially acceptable. However, it has several shortcomings. First, the time to detection (TTD) appears to be delayed in some cases when the TTD is compared to a visual inspection of the reflectance curve. In other words, the detection occurs later in the exponential growth phase (see FIG. 2 and the description that follows) than what would be expected. Second, false positive results are known to occur as a result of events such as temperature effects from loading relatively cold bottles, re-loading bottles in different cells in the incubator, and bottles being moved within the same cell. Third, false negative results are known to occur in the case of a delayed loading of bottles. A false negative result is observed when only the upper portion of the exponential phase is detected or the stationary phase is not at a reflectance level high enough to trigger the initial reflectance value positive threshold. Fourth, the algorithm logic is considered complex, difficult to understand, and difficult to maintain.

Other prior art of interest relating generally to the detection of microorganisms in a biological sample includes the following patents: U.S. Pat. Nos. 5,770,394, 5,518,923; 5,498,543, 5,432,061, 5,371,016, 5,397,709, 5,344,417, 5,374,264, 6,709,857; and 7,211,430. The following patent documents are also of potential interest: U.S. Pat. Nos. 7,991,558; 7,668,663; US 2009/0119020; US 2011/0029252; US 2011/0208432; US 2009/0287754 and US 2010/0070190.

In detection instruments such as the BacT/ALERT 3D and similar instruments, once the blood culture bottle has been tested positive for microorganism presence, it is difficult to obtain a high level of characterization of the microbial agent, or identification of the species of the microbial agent, due to the interference of blood components and artifacts of the disposable system (e.g., bottle) containing the sample. Therefore, current methods use a bottle or other suitable disposable container and a related instrument for natural growth and detection of a microorganism in the sample, as described above. Once the instrument indicates that the bottle is positive for presence of a microbial agent, according to current methods the "positive" bottle is manually retrieved from the instrument and a portion of the sample is manually removed from the bottle and cultured on an agar plate. The plate is manually placed in an incubator and periodically inspected for growth of a subculture of the microorganism. After the subculture has grown sufficiently, a sample of the culture is taken from the plate and placed in a test tube. The test tube is then introduced into yet another instrument for identification testing via a disposable test sample card having a multitude of individual wells. The disposable test cards are known in the patent literature, see e.g., U.S. Pat. Nos. 4,118,280, 3,963,355, 4,018,652; 4,116,775 and 4,038,151, 5,609,828, 5,746,980, 5,766,553, 5,843,380, 5,869,005, 5,916,812, 5,932,177, 5,951,952, and 6,045,758, the entire content of which is incorporated by reference herein.

The test sample card is then processed in an analytical instrument known in the art as the VITEK 2 instrument of the assignee. The VITEK 2 instrument incubates and periodically reads the wells of the test sample card with a reader unit. Growth of the sample in one or more of the wells of the cards results in identification of the microbial agent. The VITEK 2 instrument is described in the patent literature, see e.g., U.S. Pat. Nos. 5,762,873 and 6,086,824, the content of which is incorporated by reference herein.

This entire process from the time of introducing the sample into the blood collection bottle to culture, detection of microorganism presence, and then identification of the microorganism by the VITEK 2 instrument typically takes 2-5 days. The identification steps alone, occurring after positive bottle detection, typically occupy 1-3 of these days.

Substantial, and potentially life-saving, clinical benefits for a patient are possible if the time it takes for detection and identification of a microbial agent in a blood sample and reporting the results to a clinician could be reduced from the current 2-5 days to less than one day.

In a related application of the applicant's assignee, published as U.S. 2011/0281291, methods for identifying a microbial agent in a specimen container are disclosed. In the present disclosure, methods are disclosed for detecting whether microbial growth in a sample container is occurring, thereby indicating that an agent is present in the sample. The methods reduce the time required to make this initial determination. Because the initial determination is made earlier, the second step of identifying the agent (such as described in U.S. 2011/0281291) can be initiated earlier than otherwise possible. This invention thus contributes to an overall reduction of the amount of time needed for detection and identification of the microbial agent. Moreover, the methods of this disclosure overcome the deficiencies of current detection algorithms.

SUMMARY

A method and system for determining whether microbial growth is occurring in a specimen container is described.

The methods uses measurement data points (intensity, time) from a system that obtains measurements from the specimen container, such as for example a system disclosed in U.S. Pat. Nos. 5,856,175 and 5,164,576.

The method has several unique features, one being that the method uses two different techniques operating in parallel to detect organism growth within the specimen container. The first is a measure of data point-to-point variation. This method is applied to differentiate between measurement error, or data noise, and biological activity. The second is a measure of variations in the relative area under a plot of microorganism growth as a function of time (using signal intensity as a proxy for growth), or "growth curve" herein. This method is sensitive to the detection of inflection points in the test curve, and therefore to early detection of microbial growth. Both analytical methods include a processing step to determine whether the container is positive for growth from the input measurement data.

The two methods evaluate the measurement data points in parallel to minimize the risk of a false negative or false positive test interpretation. (A negative test result implies that organism growth was not detected. A positive test result implies that organism growth has been detected.) In one embodiment, the point-to-point variation method identifies measurement errors and responsively limits the ability of variations in the relative area under the growth curve method to determine a positive condition during the measurement error condition. The relative area under the growth curve method is the more sensitive method to detect biological activity if the data are free of measurement errors. By applying the point-to-point variation approach simultaneously, the risk of an incorrect interpretation of the curve due to the measurement of non-biological events is minimized and the advantages of using the relative area under the curve method can be fully realized.

Preferred embodiments of the method incorporate the use of real-time decision thresholds calculated using the input test data. This approach is robust to variation between measurement platforms, test media, and test organisms as compared to the use of pre-defined decision thresholds.

Additionally, in the illustrated embodiments the method does not require a complex data smoothing process. Methods that smooth data can delay the interpretation of the test and/or reduce the sensitivity of the algorithm.

In another aspect, a system for determining whether microbial growth is occurring within a specimen container is provided. The system includes an apparatus for incubating the specimen container and a measurement system obtaining a series of measurement data points while the specimen container is incubated and storing the data points in a machine-readable memory. The series of measurement data points represents a growth curve of microbial growth within the specimen container. The system further includes a programmed computer performing in parallel analytical methods (a) and (b), namely:

(a) an analysis of variation in successive data points in the series of measurement data points, and (b) an analysis of changes in the area under the growth curve between sets of data points in the series of measurement data points, wherein both analytical methods (a) and (b) include a processing step for determining a positive condition of microbial growth within the container from the measurement data points.

Both the point-to-point variation method and the relative area under the growth curve method are believed to be unique, novel and patentable. Both methods have utility alone, or in combination with other methods for determining microbial growth.

Therefore, one further aspect of this disclosure is directed to the data point-to-point variation method for determining whether microbial growth is occurring within a specimen container containing a sample. The method comprises the steps of:

incubating the specimen container;

obtaining a series of measurement data points while the specimen container is incubated and storing the data points in a machine-readable memory, the series of measurement data points representing a growth curve of microbial growth within the specimen container;

analyzing the variation in successive data points in the series of measurement data points with respect to a decision threshold, and if the variation in the successive data points exceeds the decision threshold a predetermined number of times for successive measurement data points, reporting the specimen container as positive for microbial growth.

In some embodiments, the series of measurement data points are obtained from a colorimetric sensor contained within the specimen container. However, the method is applicable for use with other methods, including methods monitoring changes in $CO_2$ concentration, pH or other value from the specimen container or its contents which are a proxy for microorganism growth.

In one embodiment, the decision threshold is calculated from the measurement data points. In another possible configuration, the method includes the step of determining from the measurement data points a spike in the measurement data points and responsively placing a constraint on a second method for determining microbial growth in the specimen container from the measurement data points. For example, the second method may be one based on colorimetric sensor readings, e.g., relative area under the curve method, a method determining growth from pH readings, etc.

The sample for which the method can be used can take any suitable form, including food samples, environmental samples, or samples from a human patient, e.g., blood or urine.

In another aspect, the invention can take the form of an improvement to a microbiological testing machine operative to receive a plurality of specimen containers, incubate the containers, and obtain a series of measurement data points from the specimen containers. The improvement is providing a processing unit in the machine operative to determine whether the containers are positive for microbial growth using the data point-to-point method. In still another aspect, the method can take the form of a programmed computing device containing machine-readable instructions for performing the data point-to-point method.

In still another aspect, a method is provided for determining whether microbial growth is occurring within a specimen container containing a sample using the relative area under the curve method. This method includes the steps of:

(a) incubating the specimen container;

(b) obtaining a series of measurement data points while the specimen container is incubated and storing the data points in a machine-readable memory, the series of measurement data points representing a growth curve of microbial growth within the specimen container;

(c) calculating the area under the growth curve for a pair of measurement data points;

(d) calculating the area under the growth curve for a second pair of measurement data points;

(e) calculating the percent difference in the area under the growth curve calculated at steps (c) and (d);

(f) determining whether the percent difference calculated at step (e) is greater than a decision threshold;

(g) if step (f) is affirmative, repeating steps (c), (d), (e), and (f) for successive pairs of measurement data points until the number of successive pairs of measurement data points having a percent difference calculated at step (f) above the decision threshold is greater than a predetermined limit; and (h) responsively reporting the specimen containers as positive for microbial growth.

As was the case with the data point to point method, the series of measurement data points can be obtained in a variety of testing formats where the measurement data points are a proxy for growth, e.g., the measurement data points are obtained from a colorimetric sensor contained within the specimen container.

In preferred embodiments the decision threshold is calculated from the measurement data points, and thus is robust to variation between measurement platforms, test media and sample types. The method can be used with a variety of sample types, including food, environmental and clinical samples, including samples obtained from a human patient such as blood or urine.

In another aspect, the invention can take the form of microbiological testing machine operative to receive a plurality of specimen containers, incubate the containers, and obtain a series of measurement data points from the specimen containers. The machine includes processing unit in the machine operative to determine whether the containers are positive for microbial growth using the relative area under the growth curve method. In still another aspect, the method can take the form of a programmed computing device containing machine-readable instructions for performing the relative area under the growth curve method.

Another aspect of this disclosure is directed to a methodology for identifying a specimen container as being positive for microbial growth and thus presence of the microbial agent in the situation where the container is incubated for an unusually long period of time prior to installation of the container in the detection system incorporating the present inventive methods. In particular, the point-to-point and relative area under the curve methods, described in summary fashion in this summary and in detail below, are able to interpret data measurements from the container detection system under typical clinical use—namely where the test bottle is inoculated with the specimen and bottle is immediately loaded into the system. However, some laboratories will hold the inoculated bottle (possibly in a refrigerated condition) for an extended period of time before loading the bottle into the system. The delay in loading can result in an incomplete reflectance or growth curve. By incomplete, we mean all of the lag phase and all or part of the exponential phase in the "typical" growth curve (FIG. 2) can be missing. A methodology, referred to below interchangeably as the "early incubation" or "late entry" methodology, provides a separate analysis of the data designed specifically for this so-called delayed entry testing. This methodology can be performed in parallel with the "point to point" variation and/or "relative area under the growth curve" methodologies, so that a container is correctly identified as positive regardless of whether or not the container was subject to delayed entry into the detection system. Alternatively, this method can be performed alone, for example in the situation where it is known that some extended period of time has elapsed after inoculation of the sample into the container before the container is introduced into the detection system.

Three different alternative methods can be used in early incubation detection algorithm to identify a container as being positive for microbial growth, including a first method calculating a mean reflectance values and comparing to a threshold, a second method using mean point-to-point value and comparison to a threshold, and a third method in which the number of consecutively increasing point-to-point values are counted and compared to a specified threshold value. In one possible embodiment, all three methods are performed in parallel on a series of time-stamped measurements from the container.

BRIEF DESCRIPTION OF THE FIGURES

FIGS. 8B-8E are plots of read to read (point to point) variation, thresholds, and reflectance which illustrate how the point to point variation method can be used to limit, e.g., temporarily, the ability of the RAUC method to declare a positive result.

DETAILED DESCRIPTION

Methods and systems for determination of a condition of microbial growth within a specimen container are described below. The methods are applicable to a variety of testing formats for microbiological presence in a sample medium and are not considered limited to any particular format. In practice, the methods can be used in any system which monitors a parameter of the specimen container or its contents, directly or indirectly, such as for example change in pH, or CO2 concentration directly, or via indirect measurements of growth such as the monitoring of intensity measurements from a colorimetric sensor within the container.

The following discussion will use one example of a testing format which is representative of a current embodiment for the sake of example and not limitation, namely the testing format of a colorimetric sensor incorporated into a bottle-like container that is regularly interrogated using an illumination device and a photodetector, see U.S. Pat. Nos. 5,856,175 and 5,164,576, the content of both of which is fully incorporated by reference herein. A modified version of this arrangement is described in U.S. application Ser. No. 13/352,428 filed Jan. 18, 2012, the content of which is incorporated by reference.

Figure 1:
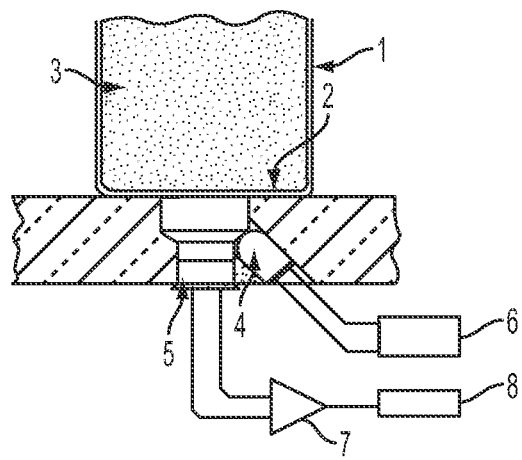
FIG. 1 is an illustration of a prior art arrangement of a system for monitoring growth of an unknown microbial agent within a specimen container which may be used in conjunction with the present methods.

The basic colorimetric sensing system described in the '175 and '576 patents is shown in FIG. 1 of the appended figures. A red Light Emitting Diode (LED) 4 directs light onto the bottom of a specimen container or bottle 1 containing a sample medium (e.g., blood or plasma) and possibly an unknown microbial agent. The bottle typically includes a growth medium along with the sample, and the arrangement of FIG. 1 is in incubation environment during the testing of the bottle for microbial growth. A colorimetric sensor 2 is deposited onto the bottom of the bottle 1 at the time of manufacture. The colorimetric sensor is known in the patent literature cited previously and will not be described further. The LED light impinges on the sensor at a 45 degree angle relative to the bottom surface of the bottle 1. The majority of the light penetrates the structure of the bottle and impinges on the colorimetric sensor 2. Part of the light will reflect off the plastic bottle material and sensor 2 at 45 degrees to the bottom surface of the bottle, but in an opposite direction to the impinging light (e.g. the angle of reflection is equivalent to the angle of incidence). Much of the remaining light is scattered from the surface and interior of the sensor. The sensor 2 changes its color as the percentage of $CO_2$ in the bottle varies, the color varies from blue to yellow, respectively. A silicon photodetector 5 "stares" (i.e., continuously monitors the scattered intensity signal) at the region in the sensor 2 where the light from the LED interacts with the sensor. The intensity of the scattered light that is detected by the photodetector is proportional to the $CO_2$ level within the bottle 1. FIG. 1 also shows the associated electronics including a current source 6, current-to-voltage converter 7 and low pass filter 8. A series of measurement data points (intensity, incubation time) in digital form are stored in memory and used by a computer (e.g., general purpose computer, workstation or central processing unit included with the system of FIG. 1) to determine whether microbial growth has occurred within the specimen container as explained herein.

Figure 2:
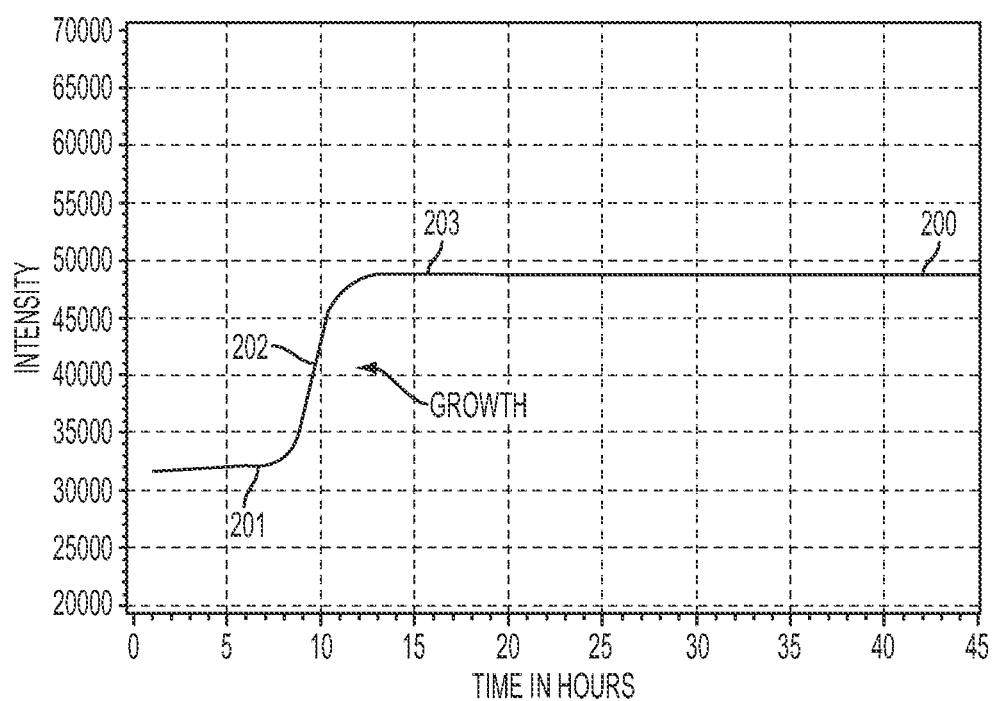
FIG. 2 is a plot of microbial growth with the container as a function of incubation time; the growth curve is represented as intensity measurements obtained from the detector of FIG. 1.

The methods of this disclosure are designed to evaluate test or growth curves and determine whether the curve is indicative of organism growth or not. The inputs to the methods are a test response value (e.g., intensity value from a photodetector) and the corresponding incubation time at which the value was obtained. An assumption is made that the growth curve will exhibit a typical shape when an organism is present in the sample. The "typical" growth curve shape is shown in FIG. 2 as a plot 200 of intensity measurements as a function of time. The plot 200 will contain a least two of the following: a lag phase 201, an exponential growth phase 202, and stationary phase 203. Typically, the lag 201 and exponential growth phases 202 are present in containers containing the microbial agent, although in practice they may not in practice exactly match the "typical" curve shown in FIG. 2 and measurement errors of one sort or another may arise as well. These measurement errors are compensated for, as explained later and in conjunction with FIGS. 11 and 12.

The transition of the plot between the lag phase 201 and the exponential growth phase 202 is of importance here, as the exponential growth phase does not normally occur in conditions of no microbial growth. The methods of this disclosure achieve a detection of this transition early on. The method has several unique features, one being that the method uses two different analytical methods operating in parallel to detect organism growth within the specimen container. The first analytical measure is a measure of data point-to-point variation. This analytical method is performed to differentiate between measurement error, or data noise, and biological activity. The second analytical method incorporates measurements of relative area under a plot of microorganism growth as a function of time (using signal intensity as a proxy for growth), or "growth curve" herein, and in particular changes to the relative area under the curve (RAUC) as a function of time. This technique is sensitive to the detection of inflection points in the test curve, and in particular the inflection point in FIG. 2 between the lag phase 201 and the exponential growth phase 202. The two techniques evaluate the measurement data in parallel to minimize the risk of a false negative or false positive test interpretation. (A negative test result implies that organism growth was not detected. A positive test result implies that organism growth has been detected.)

Preferred embodiments incorporate the use of real-time decision thresholds calculated using the input test data in making a determining of positive microbial growth. This approach allows the method to be robust to variation between measurement platforms, test media, and test organisms as compared to methods which use pre-defined decision thresholds. A challenge with developing algorithms, particularly in the instant field, is making the analysis robust to sources of variation that contribute to the signal being measured. Typically, in prior art methods, absolute thresholds are specified at the time the algorithm is defined that must take into account all possible sources of variation. Conversely, the present method calculates the thresholds based on the variation in the input data. Thus, if the curve is "noisy", the thresholds will reflect the observed level of background noise. In this case, the analysis will be less sensitive. If the curve is not "noisy", the threshold for positive determining will automatically be set to be more sensitive.

Preferred embodiments of the invention do not require a complex data smoothing process operating on the test measurements. Methods that smooth data can delay the interpretation of the test and/or reduce the sensitivity of the algorithm.

Drawing upon experience from work completed for various products of the assignee, the present inventor considered various mathematical concepts when developing the instant methods. First, area under the curve is another calculation commonly used to characterize the shape of a curve along with the rate of change and acceleration. Second, it is advantageous to use relative measures when evaluating organism activity. This can compensate for the diversity of growth curve shapes observed in clinical and industry applications. Along with organism variation, relative measures can be useful to minimize the effects of system-to-system, bottle lot-to-lot, and laboratory-to-laboratory variation. Third, methods that can differentiate between organism activity and signal deviations due to process events could improve product performance. Process control concepts come to mind when considering how to distinguish between natural or random variation versus variation that can be attributed to specific factors.

A combination of these concepts led to the design of the methods described herein. Comparing the area under a growth curve from the current segment of the curve to previous segment of the curve provides a relative measure that can identify the transition from lag phase to exponential phase. Through the analysis of test data during the early stages of test bottle incubation, control limits can be constructed that allow for the interpretation of test data. The control limits, hereafter called decision limits, can be used to differentiate between random reflectance signal variation, reflectance signal changes due to system events, and increases in the reflectance signal due to organism growth.

Point to Point (Read to Read) Variation Method Overview

Figure 3:
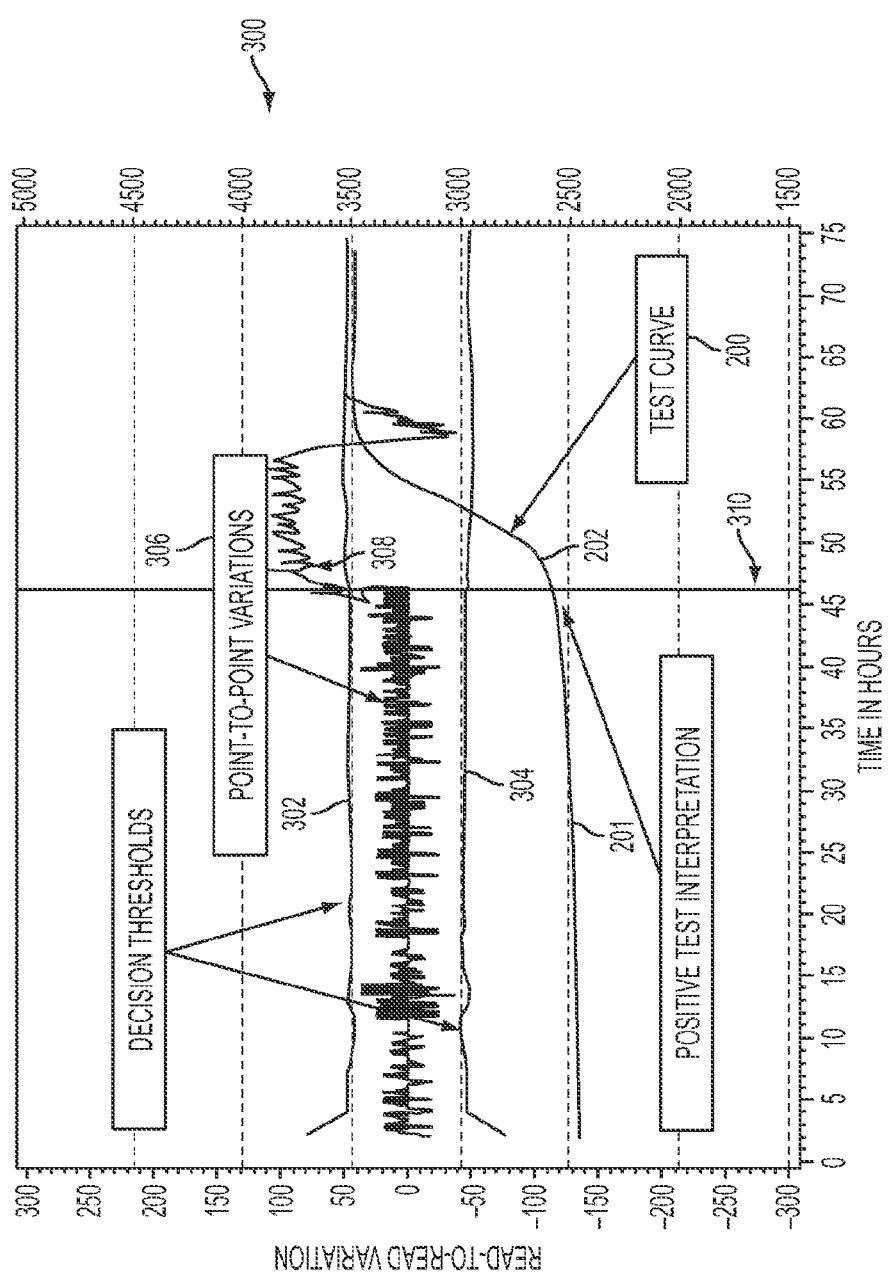
FIG. 3 is a plot of growth and point-to-point variation in the data measurements, showing that when the point-to-point variation exceeds the upper decision threshold a minimum number of times a positive test interpretation is made.
Figure 4:
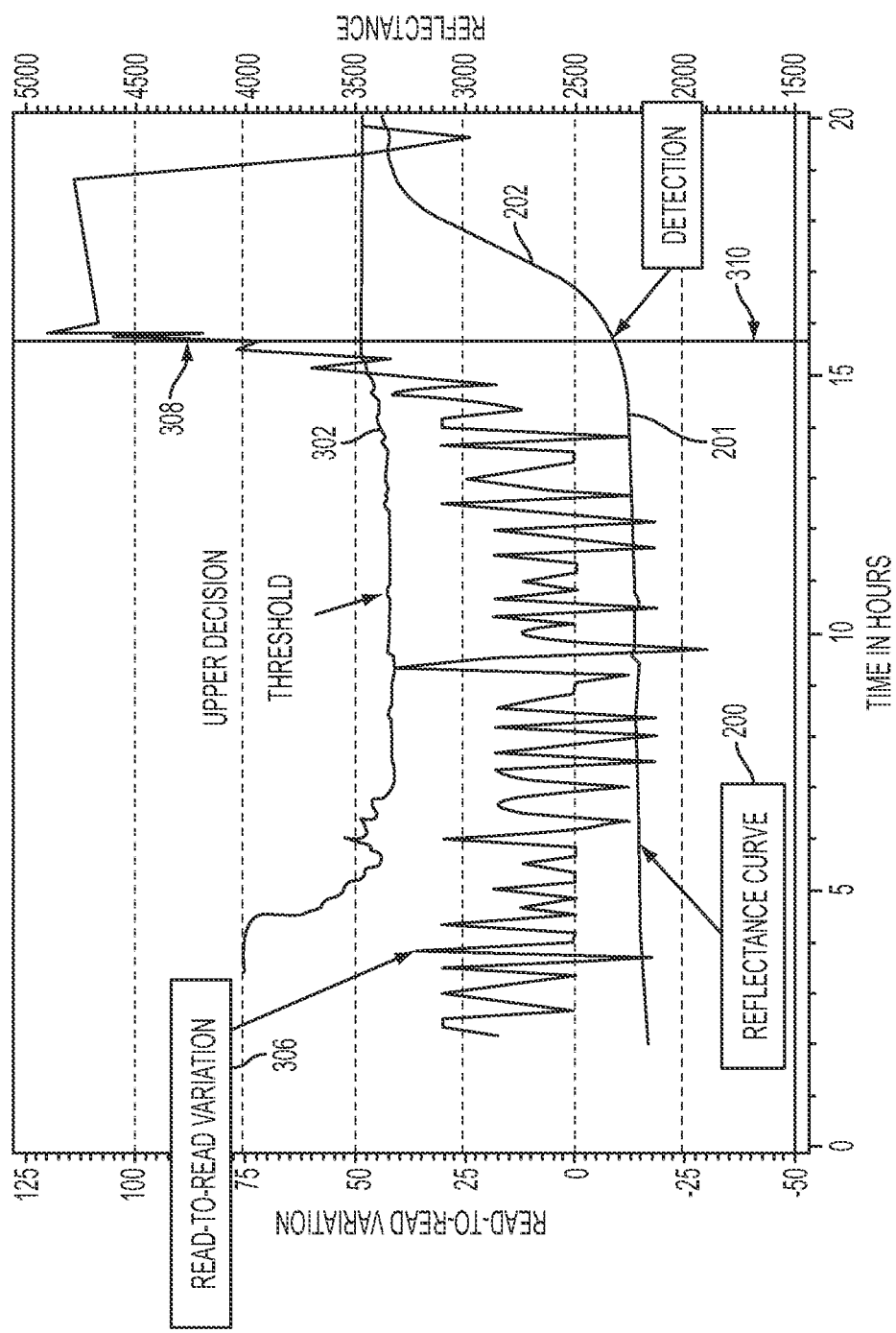
FIG. 4 is a second example of a plot of growth and point-to-point variation in the data measurements similar to FIG. 3, showing that when the point-to-point variation exceeds the upper decision a threshold minimum number of times a positive test interpretation is made.

FIG. 3 is an illustration 300 of the point-to-point variation method and how it is used to determine a positive test interpretation indicating microbial growth is occurring. FIG. 3 shows the test curve 200 (intensity from the photodetector of FIG. 1 as a function of time), upper and lower decision thresholds 302 and 304, respectively, determined from input measurement data, and a plot of point-to-point variation in the acquired measurements 306. The plot of point-to-point variation 306 exceeds the upper threshold 302 for a defined minimum number of test measurements, which is interpreted as a positive test (310) at an incubation time of 46.2 hours after the beginning of the incubation time. FIG. 4 is a second example of a data point-to-point variation plot similar to that of FIG. 3, but showing the data point-to-point variation in greater detail. Note that the plot of point-to-point variation 306 exceeds the threshold for two consecutive data points which results in the positive test interpretation 310, in this example at 15.7 hours after the start of incubation.

Note the plot of the reflectance (growth) curve 200 in FIGS. 3 and 4. The detection time (310) is right at the transition from the initial lag phase 201 and the exponential growth phase 202, indicating that in this method the positive identification is made very early in the exponential growth phase, when the growth curve first exhibits evidence of microbial growth.

Figure 5:
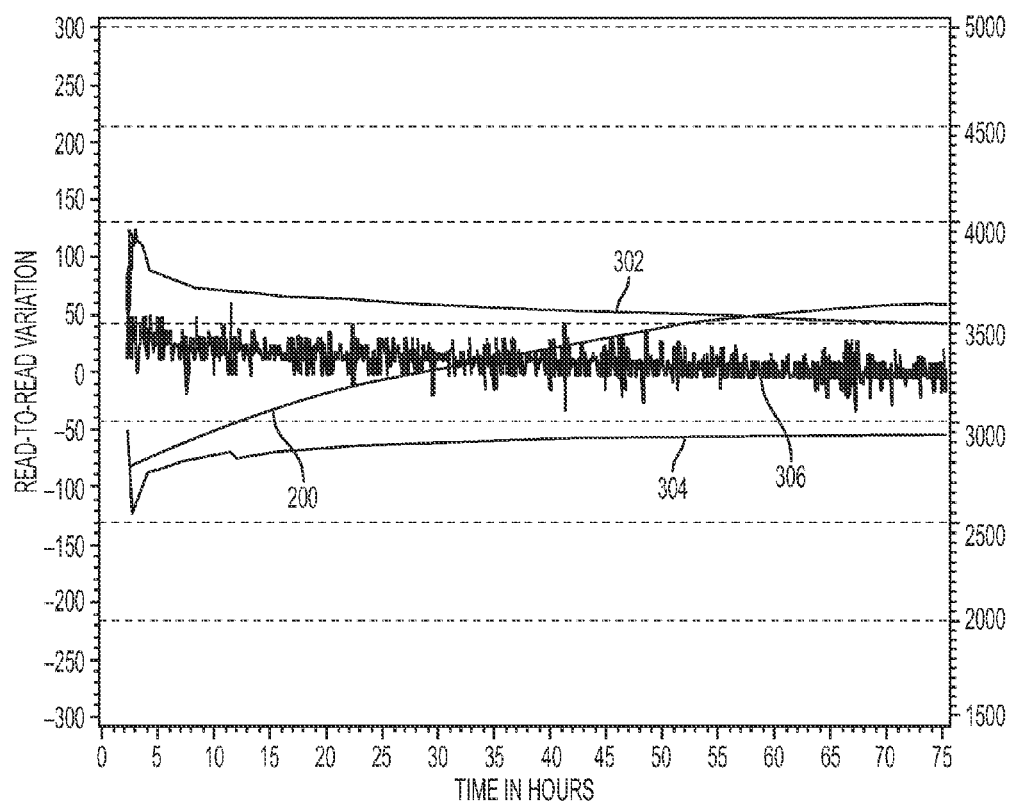
FIG. 5 is an example of a plot of growth and point-to-point variation in the data measurements in the situation where the bottle tests negative for microbial growth. Note that the data point-to-point variation plot does not exceed the upper threshold during the entire incubation period.

FIG. 5 shows the plot of growth curve (200) and data point-to-point variation under typical conditions of no microbial growth. The point-to-point variation does not exceed the upper threshold 302 and therefore no positive determination is made.

The basic idea for the point to point variation method (FIGS. 3, 4) is to differentiate between normal variation in reflectance readings and variation in reflectance that can be attributed to either organism activity or a data collection process event. To do this, upper and lower decision limits (FIGS. 302 and 304) are calculated in real time over the length of incubation based on actual readings. The limits are based on values for the standard deviation of the point-to-point (also referred to herein as "read-to-read") values, and an input parameter value, Read-to-Read (R2R) Standard Deviation Number. The standard deviation is computed with each new reflectance data point, with exceptions. As with the RAUC method (described below), the reflectance values collected during a growth curve stabilization period (typically an hour or two after incubation starts) are ignored. Also, the initial n R2R variation values must be less than the value of Initial R2R Variation Screen (an input parameter). (n is equal to the value of curve interval over which measurements are computed.) Again, these exceptions minimize the risk of calculating decision limits that are too wide and not representative of typical variation during the lag phase of organism growth.

Relative Area Under Growth Curve (RAUC) Method Overview

Figure 6:
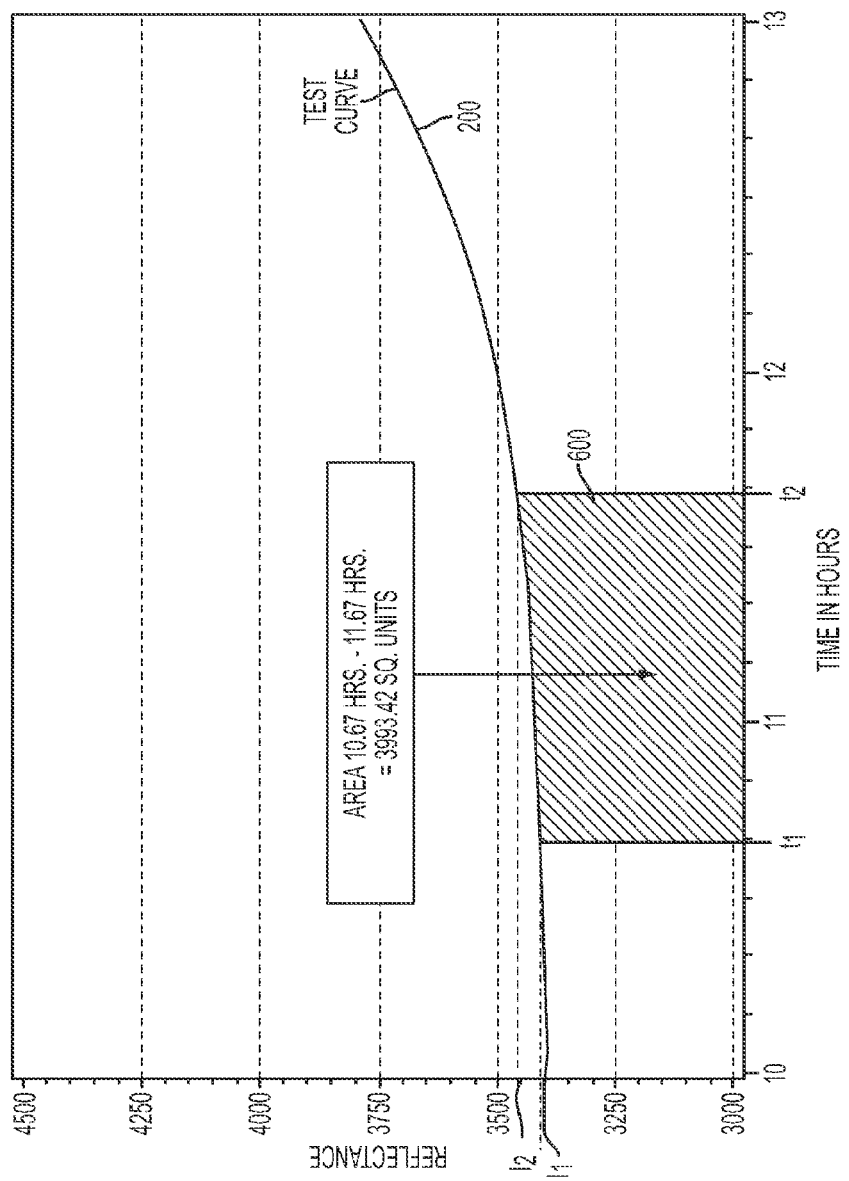
FIG. 6 is a plot showing the growth curve (intensity) as a function of incubation time, and an area under the curve between two arbitrary points in time, the area represented in arbitrary units.

As noted above, the data point-to-point variation method is optionally, but preferably implemented in parallel with a second method that monitors the relative area under the growth curve (RAUC) and in particular changes to the RAUC. FIG. 6 shows an example of a growth curve 200 and two incubation times $t_1$ and $t_2$. The area under the curve 600 between t1 and t2 is calculated using a trapezoidal approximation method. Provided $t_1$ and $t_2$ are sufficiently close to each other the curve 200 approximates a straight line and the area A (600) can be calculated according to the formula:

$$A = \frac{1}{2} \times (I_1 + I_2) \times (t_2 - t_1)$$

where $I_1$ is the intensity measurement at time $t_1$ and $I_2$ is the intensity measurement at time $t_2$.

Figure 7:
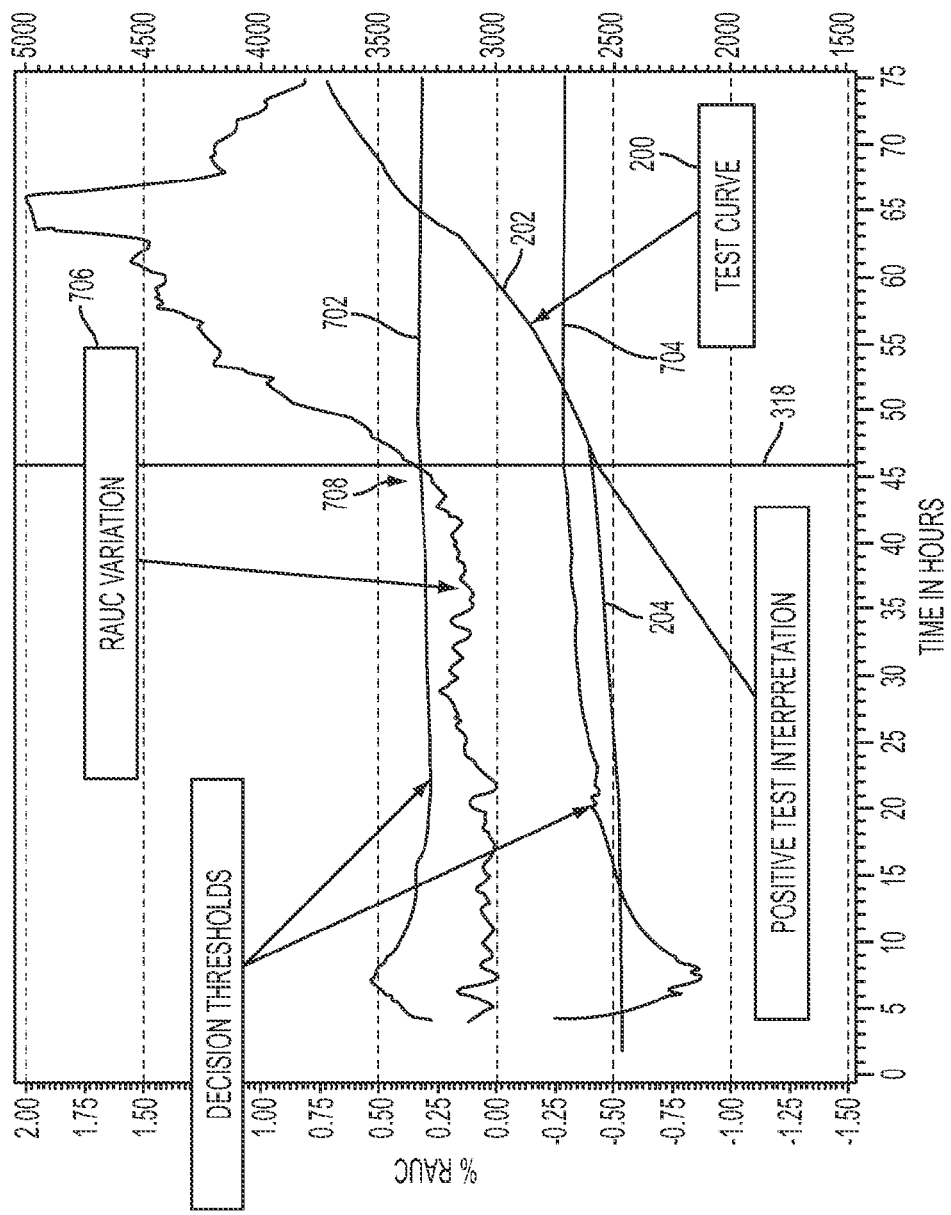
FIG. 7 is a plot of the growth curve, upper and lower decision thresholds, and relative area under the curve variation (RAUC) as a function of incubation time, showing that a positive test interpretation is made after the RAUC variation plot exceeds the upper decision threshold a minimum number of times.

As will be explained below, the RAUC method monitors changes in the relative area under the curve, termed "RAUC variation" herein. FIG. 7 shows a plot of the test (growth) curve 200, RAUC variation 702 and upper and lower decision thresholds 702 and 704 as a function of time. Note that the thresholds 702 and 704 are calculated in real time separately from the input data and are typically not the same as the thresholds of FIG. 3. When the RAUC variation exceeds the upper threshold 702 for a predetermined number of test measurements as indicated at 708 in FIG. 7 a positive test interpretation is made as indicated at 310. Note that in this technique the positive test interpretation is also made very early on in the transition between the lag phase 201 and the exponential growth phase 202 of the growth curve 202.

FIG. 8 is an illustration of the RAUC analysis method under conditions of a negative test. Note that the plot of RAUC variation 706 trends towards zero and does not exceed the upper threshold 702, therefore no positive interpretation is made.

Example

Figure 9A:
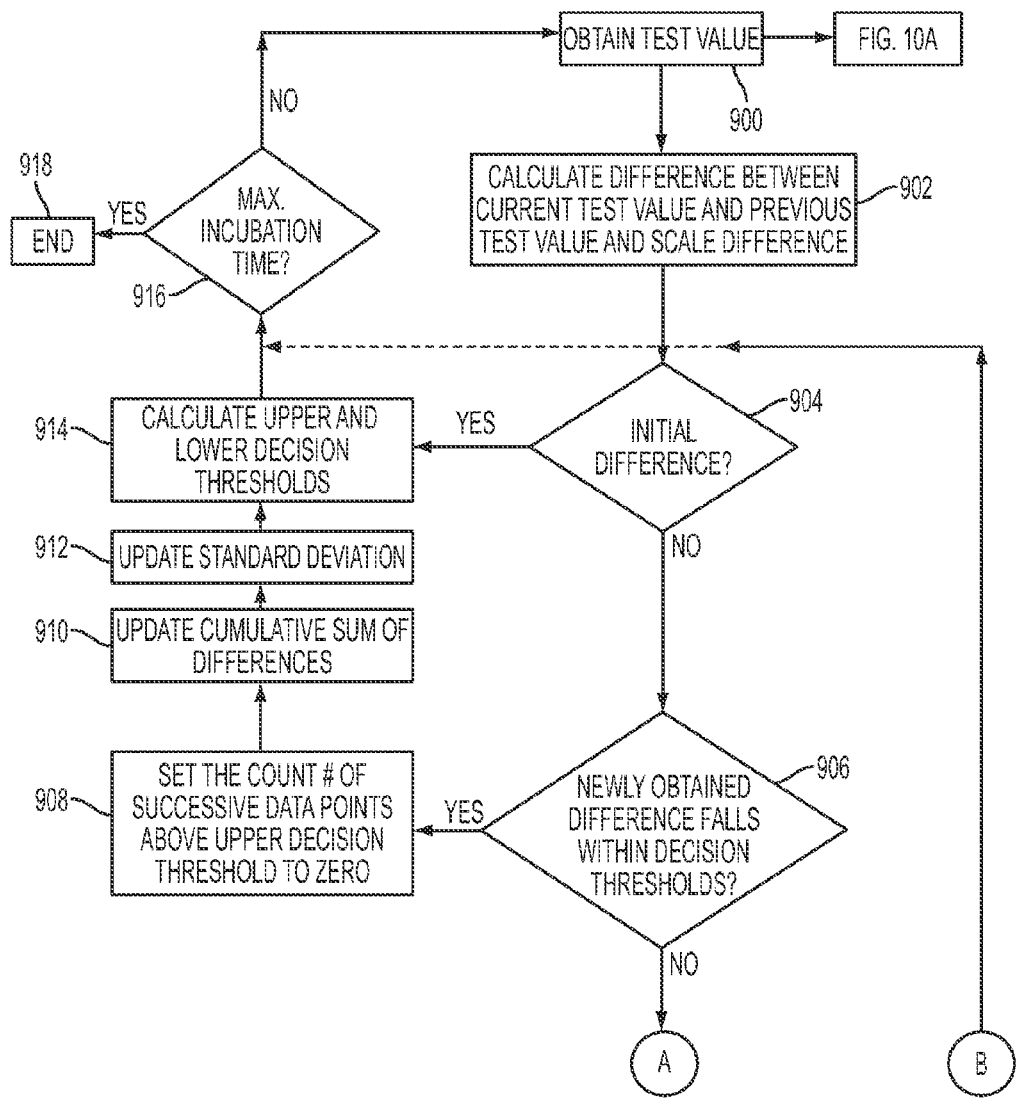
FIGS. 9A and 9B are a flow chart showing a data point-to-point variation method for determining a specimen container as being positive for microbial growth. The flow chart can be coded as a sequence of processing instructions for execution by a general purpose computing unit, such as for example a computer having access to the test measurements from the system of FIG. 1.
Figure 9B:
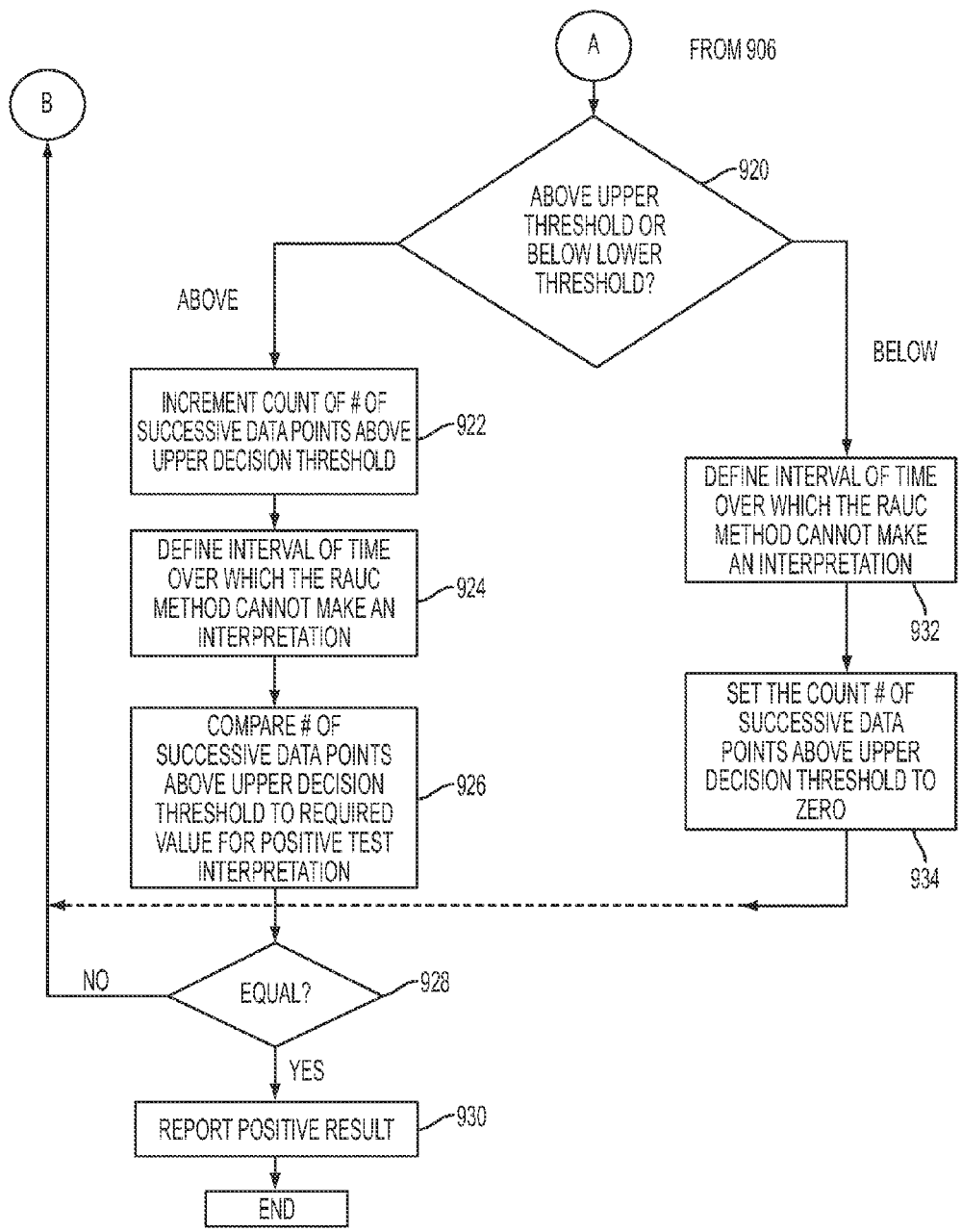
Figure 10A:
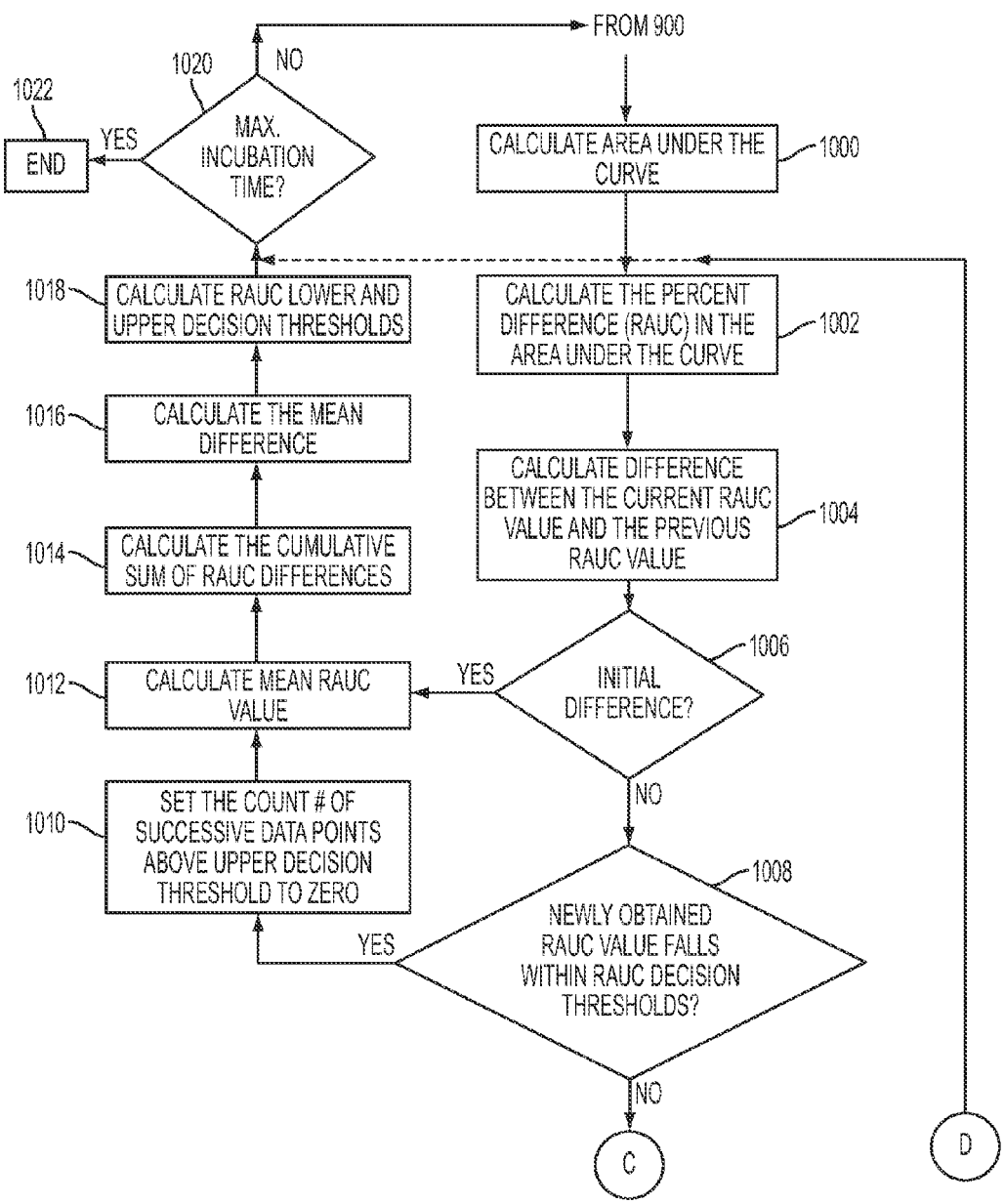
FIGS. 10A and 10B are a flow chart showing a relative area under curve (RAUC) method for determining a condition of specimen container being positive for microbial growth. The flow chart can likewise be coded as a sequence of processing instructions for execution by a general purpose computing unit, such as for example a computer having access to the test measurements from the system of FIG. 1.
Figure 10B:
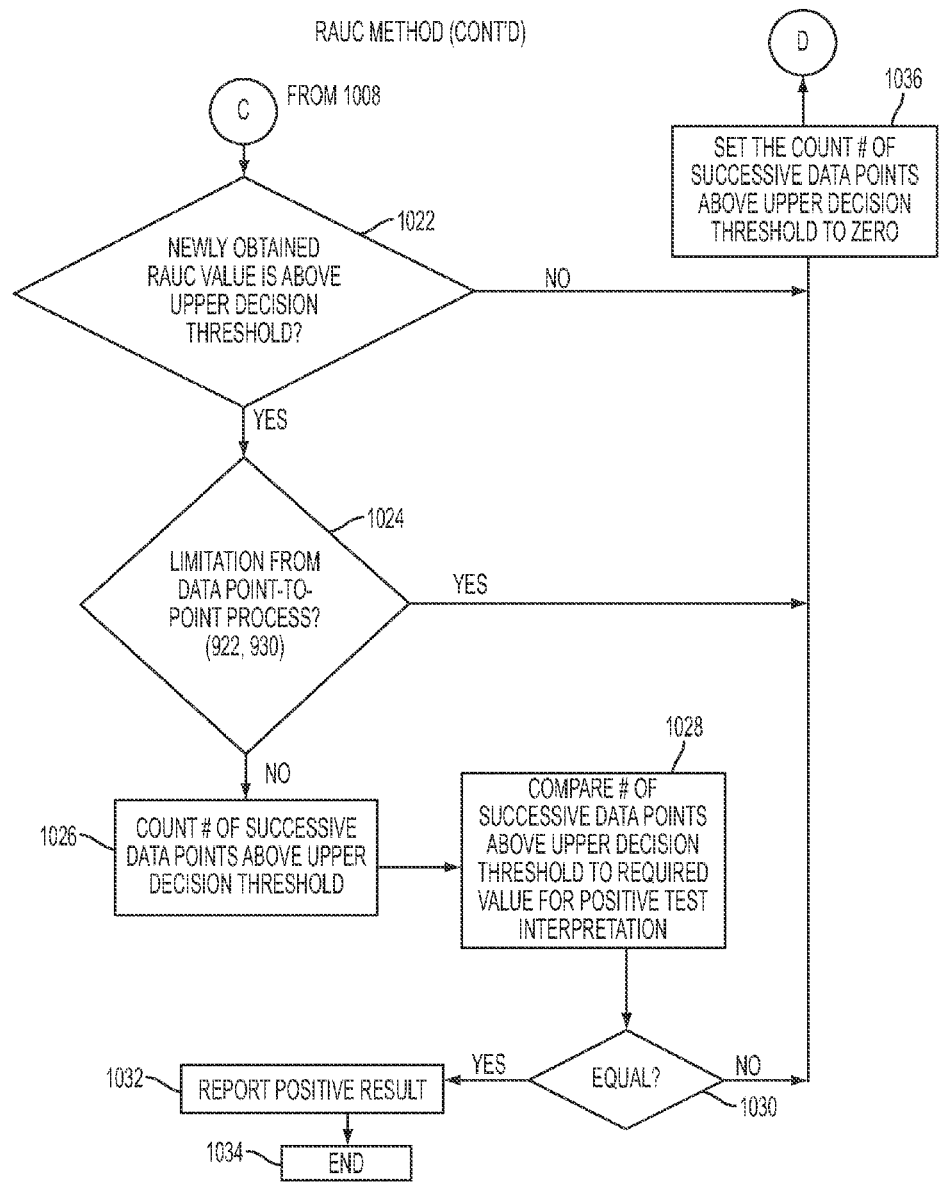

With the above discussion and FIGS. 3 and 7 in mind, this disclosure will present a detailed explanation of one example of the method in conjunctions with FIGS. 9A, 9B, 10A and 10B. FIGS. 9A and 9B are a flow chart showing the data point-to-point variation analytical method and FIGS. 10A and 10B are a flow chart showing the RAUC variation analytical method. As noted above, both methods in a preferred embodiment are performed in parallel.

Input Data and Stored Constants:

The method uses as input data the following items:

1. Ordered measurement data points (pairs) of the form (test value, time). The "test value" in this example is an intensity measurement in arbitrary units. The "time" is the incubation time (e.g., 10.35 hours). The system recording the measurement data points includes a clock and a time stamp is associated with each measurement to form the time portion of the data point.

2. A multiplication factor (positive real number) used when calculating decision thresholds 302 and 304 for data point-to-point variation technique (FIGS. 3, 9A-9B). The use of such a factor is analogous to setting a confidence level for a statistical interval.

3. A multiplication factor (positive real number) used when calculating decision thresholds 702, 704 for variation in the RAUC method (FIG. 7, 10A-10B). The use of such a factor is analogous to setting a confidence level for a statistical interval.

4. A number of test values (integer) to be used when comparing the relative area under the curve from one section of the test curve to a previous section of the test curve. This is parameter x in the following discussion.

5. Threshold values (integer) that correspond to the number of successive data points above the decision threshold that need to be observed before interpreting a test as positive. One value needs to be specified for point-to-point variation method (value "NR2RP" below), and a second value needs to be specified for relative area under the curve method (value "NRAUCP" below).

6. Period of time (positive real number that corresponds to a number of hours) during the initial stages of incubation when test values will be ignored. For some tests, a period of time is required for the test environment to stabilize. This parameter is termed CSP (curve stabilization period) herein.

7. A maximum incubation time, after which the processing stops if a positive test result has not been reported by either the point-to-point variation or the RAUC methods. If the maximum incubation time has been met without a positive test result being made the method reports a negative test result.

A high level description of the method is as follows:

Using data from incubation time after the curve stabilization period (CSP):

Repeat the following for each new data point until the curve is interpreted as positive or the maximum incubation time is observed.

For the data point-to-point analysis process, calculate the difference between two consecutive data points scaled by the time between data points (point-to-point variation).

If the calculated difference is the initial difference value, calculate the upper and lower decision thresholds If the calculated difference is not the initial value and the point-to-point variation falls within the related upper and lower thresholds, update the upper and lower thresholds using the additional information.

If the calculated difference is not the initial value and the point-to-point variation is below the lower threshold, the number of data points less than 4 times x will be labeled as unreliable data for RAUC algorithm calculations.

If the point-to-point variation is above the upper threshold, increment the number of consecutive point-to-point variation values above the upper control limit.

Also, if the point-to-point variation is above the upper threshold, the number of data points less than the value of 2 times x will be labeled as unreliable data for RAUC algorithm calculations.

If the point-to-point variation is not above the upper threshold, set the number of consecutive point-to-point variation values above the upper threshold to zero.

If the number of consecutive point-to-point variation values above the upper threshold is equal to the number of point-to-point variation values necessary to determine a positive curve (NR2RP), the curve is interpreted as positive.

For the relative area under the curve (RAUC) method, calculate the area of the trapezoid formed by two consecutive ordered measurement data points.

When sufficient data are available, calculate the relative area under the curve (RAUC) based on the value of x (area under the curve is calculated by trapezoid approximation method).

Calculate the difference between the current RAUC value and the previous RAUC value.

If the calculated difference is the initial difference value, calculate the RAUC upper and lower decision thresholds.

If more than one difference calculation has been performed and the value of RAUC falls within the related upper and lower thresholds and the data are labeled as reliable, update the upper and lower thresholds using the additional information.

If the value of RAUC is greater than the upper threshold and the data are reliable, increment the number of consecutive RAUC values above the upper threshold.

If the value of RAUC is not greater than the upper threshold, set the number of consecutive RAUC values above the upper threshold to zero.

If the number of consecutive RAUC values above the upper threshold is equal to the number of RAUC values to determine a positive curve (NRAUCP), the curve is interpreted as positive.

Turning now to FIG. 9A, a specific embodiment of the point-to-point variation method will be described. The method of FIG. 9A is coded as software instructions which are executed in a processing unit such (CPU) of a general purpose computer, workstation, or processing unit associated with the incubation and testing system of FIG. 1 or FIG. 17, described later. The method begins at step 900 of acquiring a test value in the form of (value, time).

At step 902, calculate the difference between the current test value and the previous test value and scale the difference by the interval of incubation time between the two test values. Scaling by the interval of incubation time between the two data points compensates for inconsistencies between times test values are obtained.

At step 904, determine whether the difference from 902 is the first difference value.

If yes, proceed to step 914

At step 914, calculate the upper and lower point-to-point decision thresholds (302 and 304 of FIG. 3) using read-to-read (R2R) standard deviation values as follows:

The formula for the R2R standard deviation is given by:

R2R Standard Deviation $s$=Sum(of the differences between two consecutive R2R values 1 to $n$)/$n$    (Equation 1)

Where the difference between two consecutive R2R values is

|R2Rprevious−R2Rcurrent| and $n$ is the R2R value associated with the current reflectance reading. (RAUC values to be ignored are not included in the 1 to n sequence)

The formulas for the upper and lower decision limits are given by:

Lower R2R Decision Limit(304,FIG. 3)=$ks$

Upper R2R Decision Limit(302,FIG. 3)=$-ks$

Where k is the R2R Standard Deviation Number (an input parameter), and s is the R2R standard deviation calculated per Equation 1.

If no (step 904), proceed to step 906.

At step 906, determine whether a newly obtained difference (step 902) falls within the existing upper and lower decision thresholds calculated at step 914.

If yes, the difference falls within the upper and lower decision thresholds, proceed to steps 908, 910, 912, 914 and 916.

At step 908, set the count of successive data points above the upper decision threshold to zero.

At step 910, update the cumulative sum of differences.

At step 912, update the standard deviation (s, equation 1).

At step 914, calculate the upper and lower decision thresholds as previously described.

Proceed to step 916.

If no, at step 906, the difference does not fall within the upper and lower decision thresholds, the processing proceeds to the steps shown in FIG. 9B:

At step 920 (FIG. 9B), determine whether the difference is above the upper threshold or below the lower threshold.

If above, proceed to step 922, 924, 926 and 928:

At step 922, increment the count the number of successive data points above the decision threshold by 1.

At step 924, define an interval of time over which the RAUC method cannot make an interpretation (FIGS. 10A and 10B). At this point, it is possible that a test measurement error has occurred. Therefore, step 924 prevents the RAUC method from interpreting the test curve as positive based on changes in the data not necessarily related to microbiological activity.

At step 926, compare the number of successive data points above the upper decision threshold to the input parameter value (NR2RP), the value required to indicate a positive test interpretation.

If the number of successive data points above the upper decision threshold is equal to NR2RP, (step 928), a positive result is reported at step 930.

If the number of successive data points above the upper decision threshold is not equal to NR2RP, (step 928), proceed to step 916.

If the newly obtained difference measurement is below the lower threshold (302) at step 920, proceed to step 932.

At step 932, define the interval of time over which the RAUC method cannot make an interpretation (FIGS. 10A and 10B). As mentioned above, this prevents a possible false positive interpretation.

At step 934, set the count of successive data points above the upper decision threshold to zero.

Proceed to step 916.

At step 916, compare the current incubation time to the maximum incubation time to determine whether to terminate the analysis, If yes, the current incubation time is equal to the maximum incubation time, terminate the test and the interpretation is a negative result.

If no, the current incubation time is less than the maximum incubation time, loop back to step 900. Continue the process until a positive test interpretation is obtained through the data point-to-point analysis, a positive test interpretation is obtained through the RAUC analysis, or the process reaches the maximum incubation time.

The RAUC method will now be described with reference to FIGS. 7 and 10A-10B. The processing begins by obtaining a test result data pair (900, FIG. 9A).

At step 1000, calculate the area under the curve (AUC) for the portion of the curve determined by the last 1 to x test values and the area under the curve for the portion of the curve determined by the last x to (2x−1) test values, where x is the number of test values specified in the input data.

At step 1002, calculate the percent difference (RAUC) in the area under the curve using the following RAUC=100(AUC$_{(2x-1) \text{ to } x}$−AUC$_{1 \text{ to } x}$)/AUC$_{1 \text{ to } x}$ At step 1004, calculate the difference between the current RAUC value and the previous RAUC value.

At step 1006, determine whether the difference from step 1004 is the first difference. value.

If yes, proceed to step 1012.

At step 1012, calculate the mean RAUC value.

At step 1014, calculate the cumulative sum of RAUC differences.

At step 1016, calculate the mean difference based on step 1014.

At step 1018 calculate the RAUC upper and lower decision thresholds using the following:

Upper Decision Threshold(702)=(mean RAUC)+ (multiplication factor)(mean difference)

Lower Decision Threshold(704)=(mean RAUC)− (multiplication factor)(mean difference)

[Note, the multiplication factor for calculating the RAUC decision thresholds is defined as an input parameter.]

Proceed to step 1020.

If no, at step 1006, more than one difference value has been calculated, proceed to step 1008.

At step 1008, determine whether the newly obtained RAUC value, from 1002, falls within the RAUC decision thresholds.

If yes, proceed to step 1010.

At step 1010, set the count of the number of successive data points above the upper decision threshold to zero.

At step 1012, calculate the mean RAUC value.

At step 1014, calculate the cumulative sum of RAUC differences.

At step 1016, calculate the mean difference based on step 1014.

At step 1018 calculate the RAUC upper and lower decision thresholds as described earlier.

Proceed to step 1020.

If no at step 1008, the newly obtained RAUC value does not fall within the decision thresholds, proceed to step 1022 (see FIG. 10B).

At step 1022, determine whether the RAUC value falls above the upper decision threshold If yes, proceed to step 1024

At step 1024, determine whether there is a limitation from the data point-to-point analysis process (from steps 922 or 930).

If yes, proceed to step 1036

At step 1036, set the count of the number of successive data points above the upper decision threshold to zero.

Next, proceed to step 1020. Proceeding to this step, at this point in the process, prevents the potential for a false positive interpretation of the curve due to measurement error. Additionally, the data point is not used to update the RAUC lower and upper thresholds. Thus, data from measurement error does not incorrectly inflate the evaluation of natural process variation.

If no at step 1024, proceed to step 1026

At step 1026, increment the count of successive data points above the upper decision threshold.

At step 1028, compare the number of successive data point above the threshold to the value to indicate a positive test interpretation (NRAUCP).

If equal (step 1030) to the input parameter, report a positive test result at step 1032. The process then ends (1034).

If not equal to the input parameter, proceed to step 1036.

At step 1036, set the count of the number of successive data points above the upper decision threshold to zero and then proceed to step 1020.

If no (from step 1022), the newly obtained RAUC value is not above the upper decision threshold, proceed to step 1036 and then step 1020.

At step 1020, compare the current incubation time to the maximum incubation time to determine whether to terminate the analysis.

If yes, terminate the test and the interpretation is a negative result, step 1022.

If no, the current incubation time is less than the maximum incubation time, loop back to step 1000 with the next data pair. Continue the process until a positive test interpretation is obtained through the data point-to-point analysis, a positive test interpretation is obtained through the RAUC analysis, or the process reaches the maximum incubation time.

As mentioned previously, the two methods (point to point and RAUC) preferably operate in parallel and under certain conditions the point to point method may operate to prevent the RAUC method from indicating a positive result for some period of time. As indicated by block 906 of FIG. 9A, in the point to point method, with each new data point (test value), the test value is compared to the upper and lower decision limits. When the test value is within the limits, the value is used to update the standard deviation (step 912), both decision thresholds (step 914), and the positive count is set to zero (step 908). When the test value is above the upper decision limit, the value is not used to update the standard deviation and decision limit (see FIG. 9B, steps 922, 924 and 926). Additionally, two cases need to be considered.

One case is that the increase in test values is a result of organism activity. To cover this possibility, the read to read positive count is increased by 1 (step 922). If the increase in R2R values is due to organism activity, a series of values above the upper decision limit will occur. When the R2R positive count reaches the value of the R2R Positive Number the curve is interpreted as positive, as indicated by steps 926, 928 and 930.

The second case is that the increase is due to some interfering process factor. In order to prevent a false positive result with the RAUC algorithm, a positive shift warning condition is initiated that prevents the RAUC algorithm from interpreting the curve as positive. Furthermore, reflectance data that are observed during the warning condition are not used to update the RAUC mean, standard deviation, and decision limit. The warning condition exists for a specified period of time.

If the R2R value is below the lower decision limit, it is known that a process factor has caused a decrease in reflectance. For this situation, as indicated at step 932, a negative shift warning condition is created for a specified length of time. Again, the RAUC algorithm cannot interpret a curve as positive during this warning period, and the reflectance data are not used for RAUC mean, standard deviation, and decision limit calculations.

The value of the Read-to-Read Standard Deviation Number (an input parameter used in calculating the decision thresholds, Step 914) is critical in determining optimal performance for the point to point variation and RAUC methods. When the value of this input parameter is too small, too many data points will be considered outside of normal process variation. As a result, unnecessary positive and negative shift warning conditions will be created. This can potentially eliminate the advantages of the RAUC algorithm. Values for the R2R Standard Deviation Number that are too large can result in interfering factors going undetected. Thus, the risk of false positive results would increase. Under typical data collection conditions, the RAUC algorithm is capable of detecting more subtle changes in reflectance due to organism activity than the point to point algorithm. The point to point algorithm serves a valuable function in that it can detect system events that complicate curve interpretation. Optimization of this input parameter can be optimized by a routine exercise of trial and error for a given system, type of container and sensor, etc.

Figure 8A:
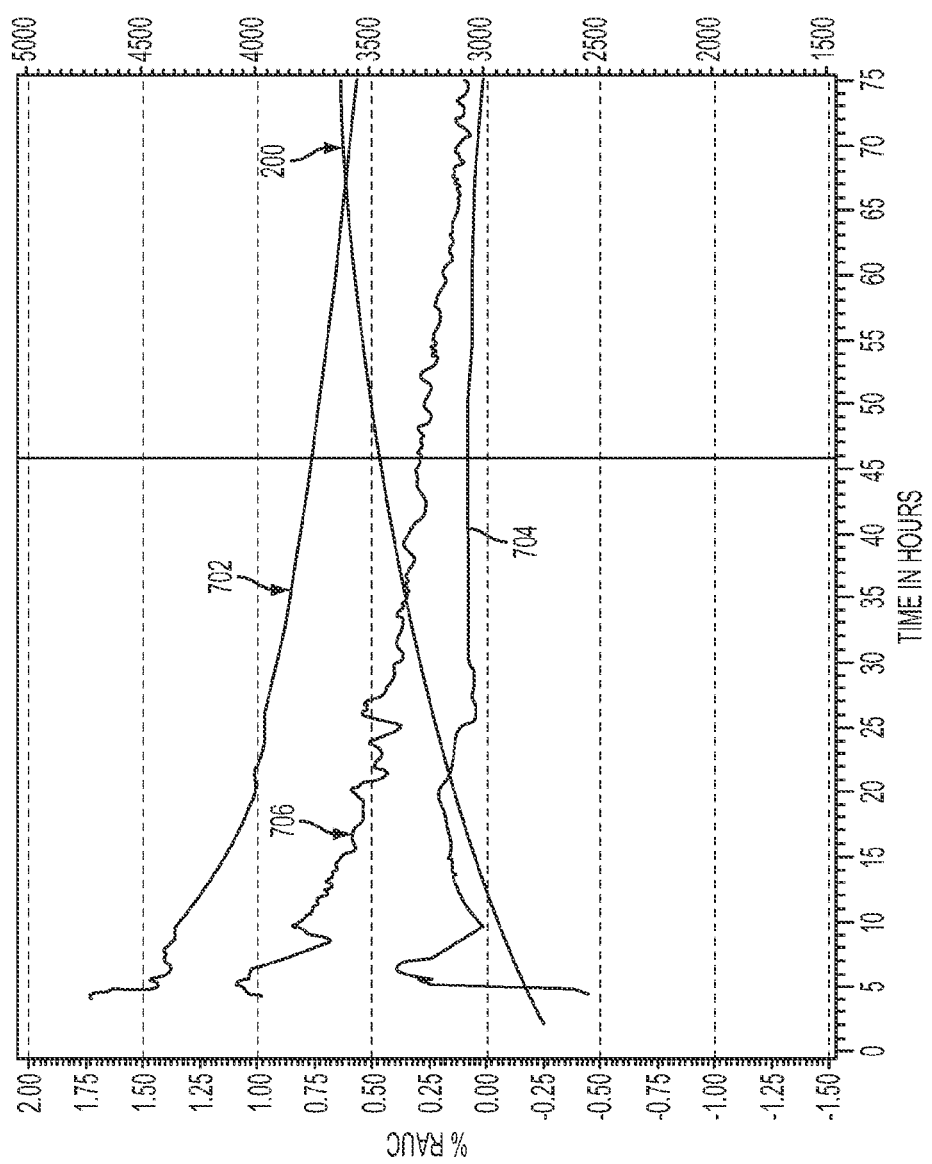
FIG. 8A is an illustration of the RAUC analysis method under conditions of a negative test. Note that the plot of RAUC variation stays within the upper and lower thresholds and trends towards a zero value.
Figure 8B:
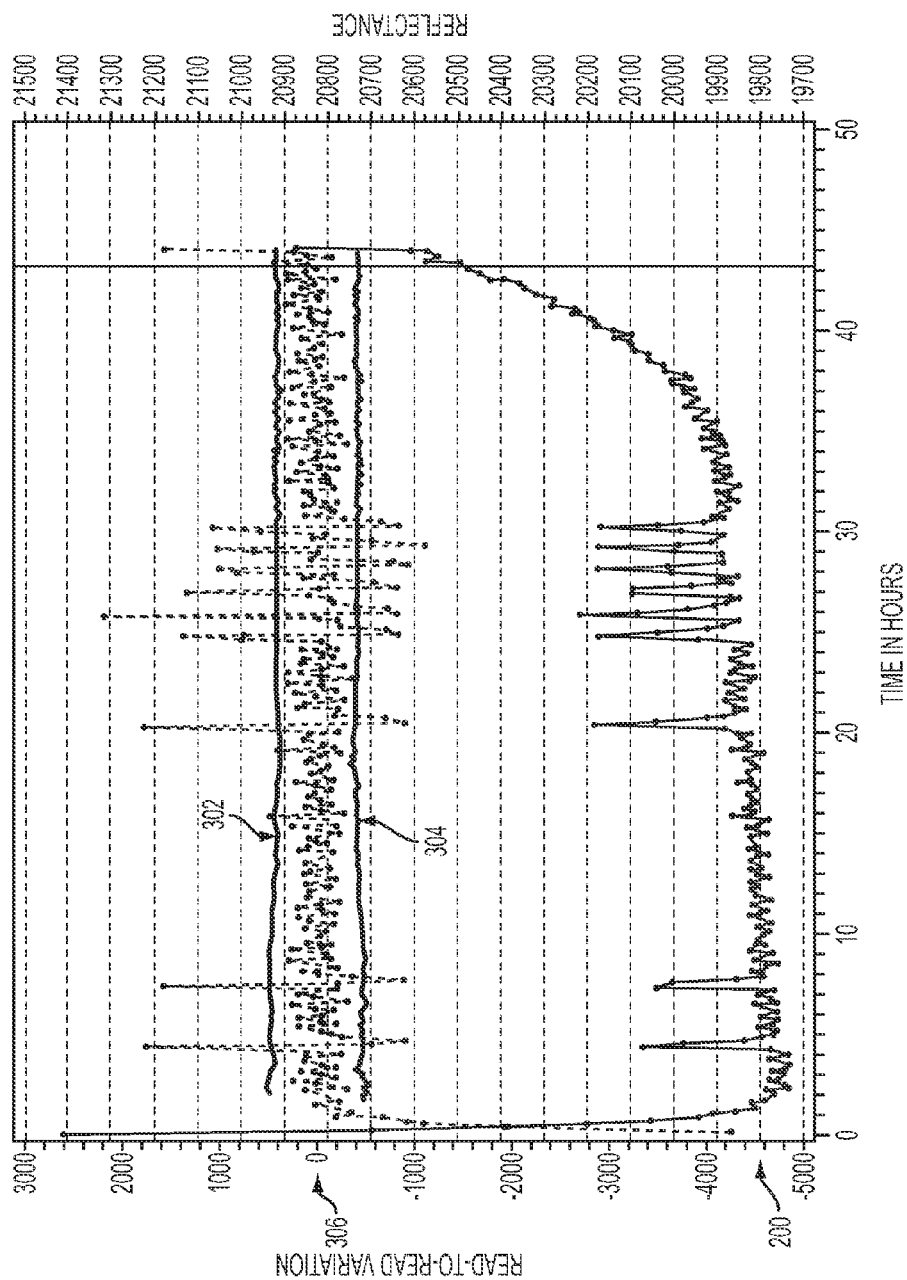
Figure 8C:
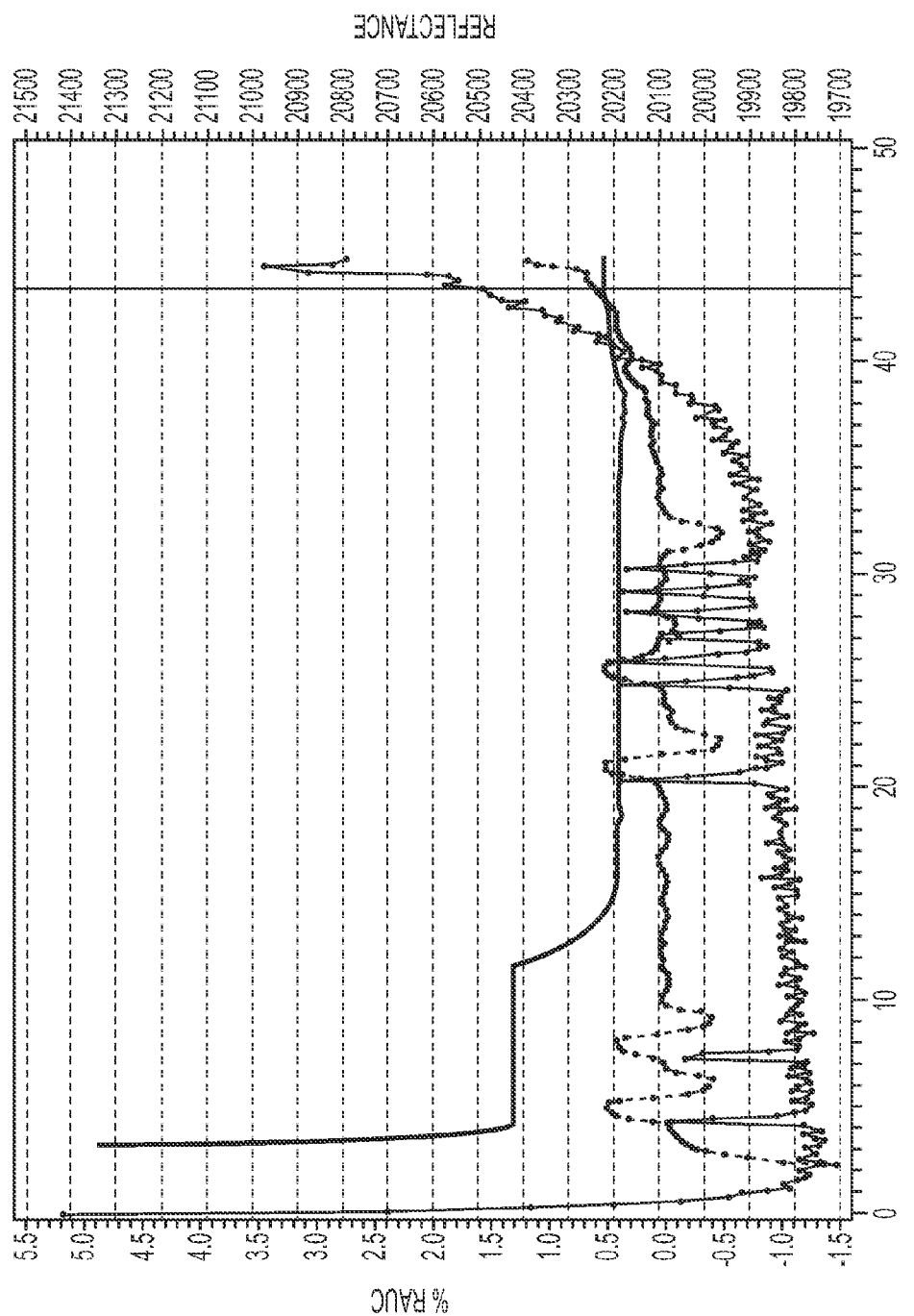

FIGS. 8B and 8C provide an illustration of the point-to-point and RAUC algorithms working simultaneously with reflectance data that contains of variation from temperature effects. FIG. 8B is a plot of the point to point variation (306, including upper and lower thresholds 302 and 304, and a test (growth) curve 202 from the reflectance measurements. Notice that the point-to-point decision limits (thresholds 302 and 304) capture only the portion of the reflectance data unaffected by temperature changes.

FIG. 8C shows that the RAUC decision limit adjusts to the data over the length of incubation taking instructions from the point to point algorithm to ignore extreme data points. Most importantly, the point-to-point algorithm invokes warning conditions at approximately hours 20 and 25 that prohibit the RAUC algorithm from interpreting the curve as positive. In the end, the curve is appropriately determined to be positive at just over 43 hours by the RAUC algorithm.

A special case is possible when the reflectance data are noisy around the inflection point between the lag and exponential phases. The point-to-point algorithm can signal a warning condition that prohibits the RAUC algorithm from declaring the curve positive when, in fact, the curve is positive. The point-to-point algorithm will eventually provide a positive result, but with a delay. In this special case, an additional condition is checked as part of the RAUC algorithm. Referring back to FIG. 8B, RAUC values affected by interfering events have the characteristic of a hump and/or dip. RAUC values associated with organism activity during the exponential phase are consistently above the decision limit for an extended period of time. If the RAUC positive count is equal to the Extended RAUC Positive Number, the curve is interpreted as positive even if a warning condition exists from the point to point algorithm.

Figure 8E:
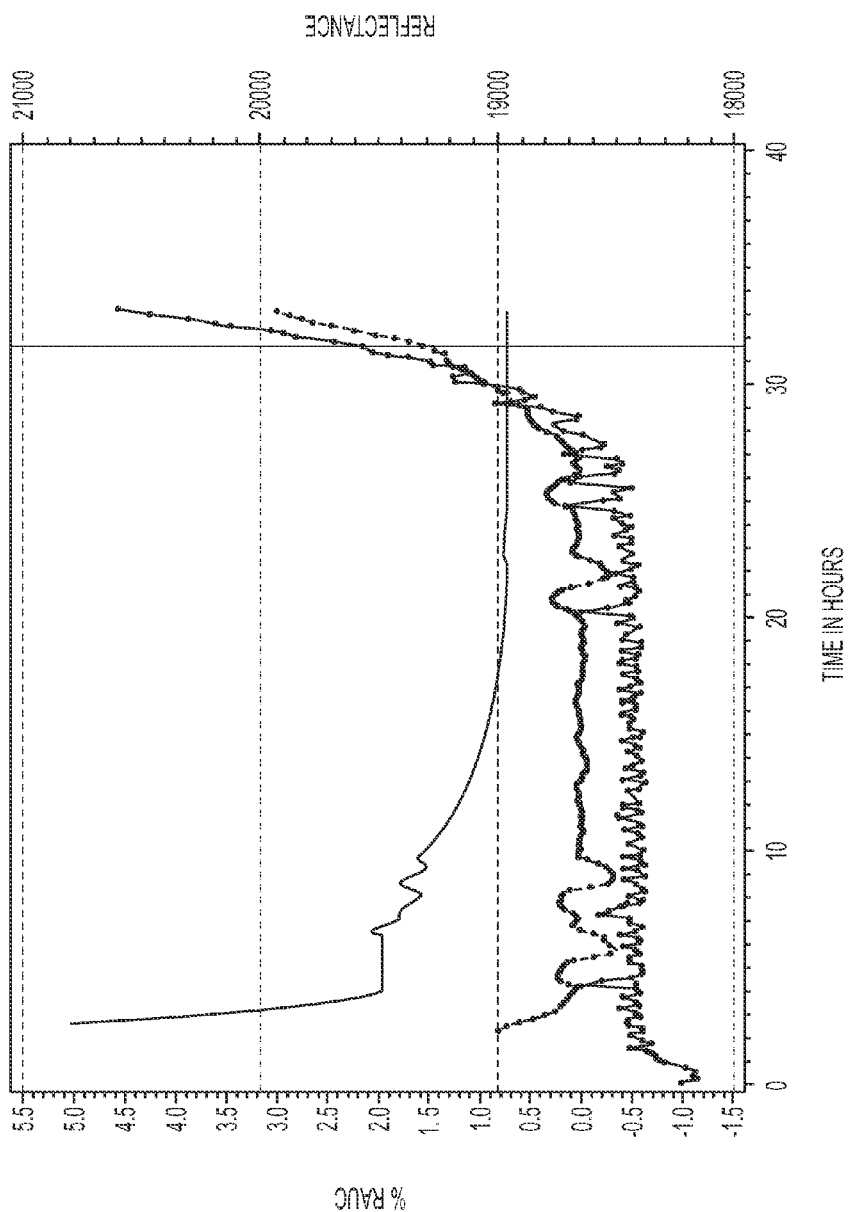

FIG. 8D provides an example of the special case. In FIG. 8C, several R2R values are above the upper decision limit after hour 25. These values create shift warnings. However, FIG. 8E shows that the RAUC values are consistently above the decision limit after hour 30, approximately. In this case the number of RAUC values above the decision threshold is sufficient to meet the have the bottle declared positive under the RAUC method.

Figure 11:
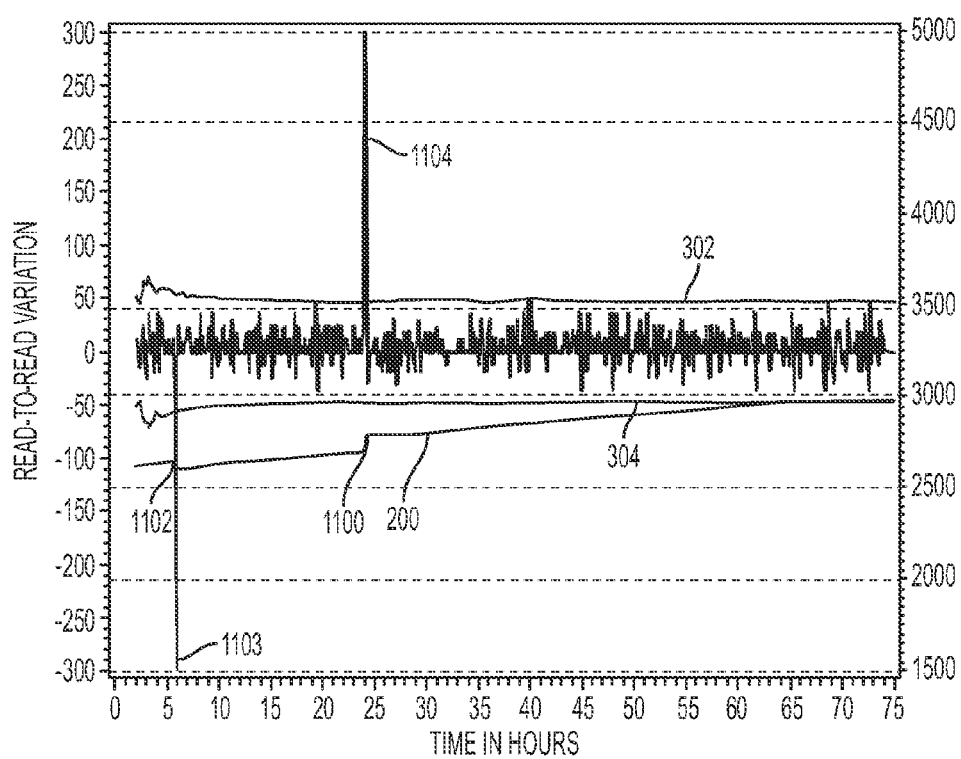
FIG. 11 is an illustration of the data point-to-point analysis method with a negative test condition and measurement errors indicated by spikes in the plot of point-to-point variation.

FIG. 11 is an illustration of the data point-to-point analysis method with a negative test, with measurement errors in the growth curve shown at 1100 and 1102, which cause spikes 1103 and 1104 in the plot of point-to-point variation. Because these spike 1104 represent a single instance above the threshold 302 and the parameter NR2RP is set at an integer greater than one (e.g., two, three or four), the measurement error does not result in a false positive interpretation.

Figure 12:
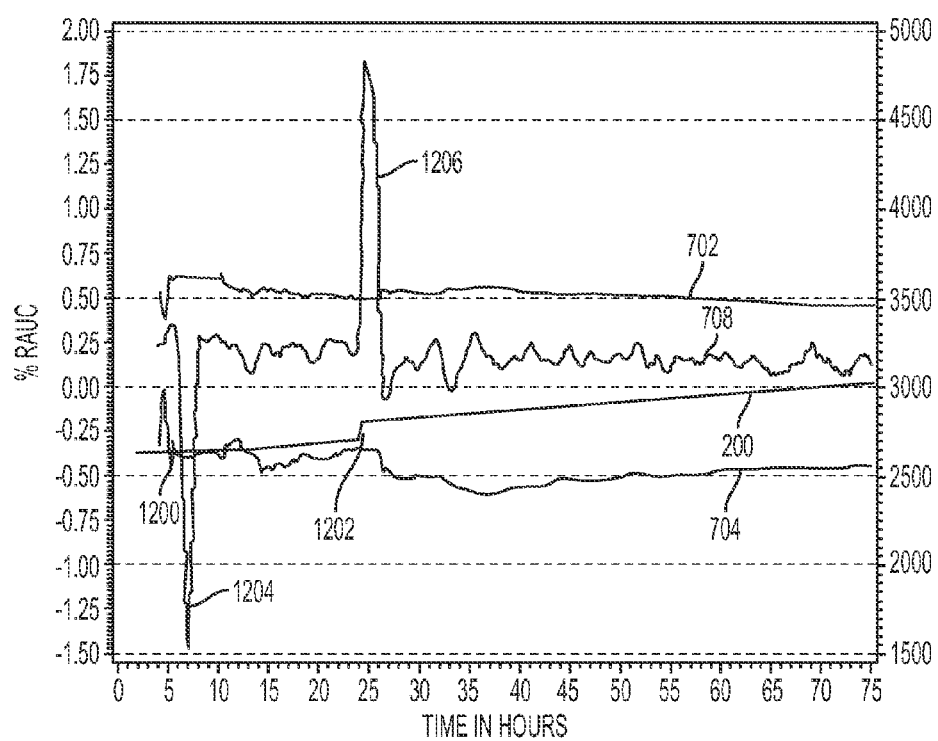
FIG. 12 is an illustration of the RAUC analysis method with a negative test condition and measurement errors indicated by spikes in the plot of RAUC variation.

FIG. 12 is an illustration of the RAUC analysis method with a negative test, with measurement errors in the growth curve indicated at 1200 and 1202, which causes spikes 1204 and 1206 in the plot of RAUC variation (708). However, there is a single spike 1206 above the threshold 702 therefore the number of successive points above the threshold 702 is one, which is less than the value needed for a positive interpretation (NRAUCP) in this example, and therefore the measurement error does not result in a false positive interpretation.

Early Incubation/Delayed Entry Methodology

As noted above, another aspect of this disclosure is directed to a methodology for identifying a specimen container as being positive for microbial growth and thus presence of the microbial agent in the situation where the container is delayed for an unusually long period of time prior to installation of the container in the detection system incorporating the present inventive methods. In particular, the point-to-point and relative area under the curve methods, described in detail above, are able to interpret data measurements from the container detection system under typical clinical use—namely where the test bottle is inoculated with the specimen and bottle is immediately loaded into the system for incubation and reading. However, some laboratories will hold the inoculated bottle (possibly but not necessarily under incubation conditions) for an extended period of time before loading the bottle into the detection system. The delay in loading can result in an incomplete reflectance or growth curve. By incomplete, we mean all of the lag phase and all, part, or most of the exponential phase in the "typical" growth curve of FIG. 2 can be missing.

A methodology, described in this section "the early incubation methodology" provides a separate analysis of the data designed specifically for this early incubation or "delayed entry" testing scenario. This methodology can be performed in parallel with the "point-to-point" variation and/or "relative area under the growth curve" methodologies explained in detail above, so that a container is correctly identified as positive regardless of whether or not the container was subject to late entry into the detection system. Alternatively, this method can be performed alone, for example in the situation where it is known that a given container is introduced into the detection system after some extended period of time has elapsed after inoculation of the sample into the container.

Figure 13:
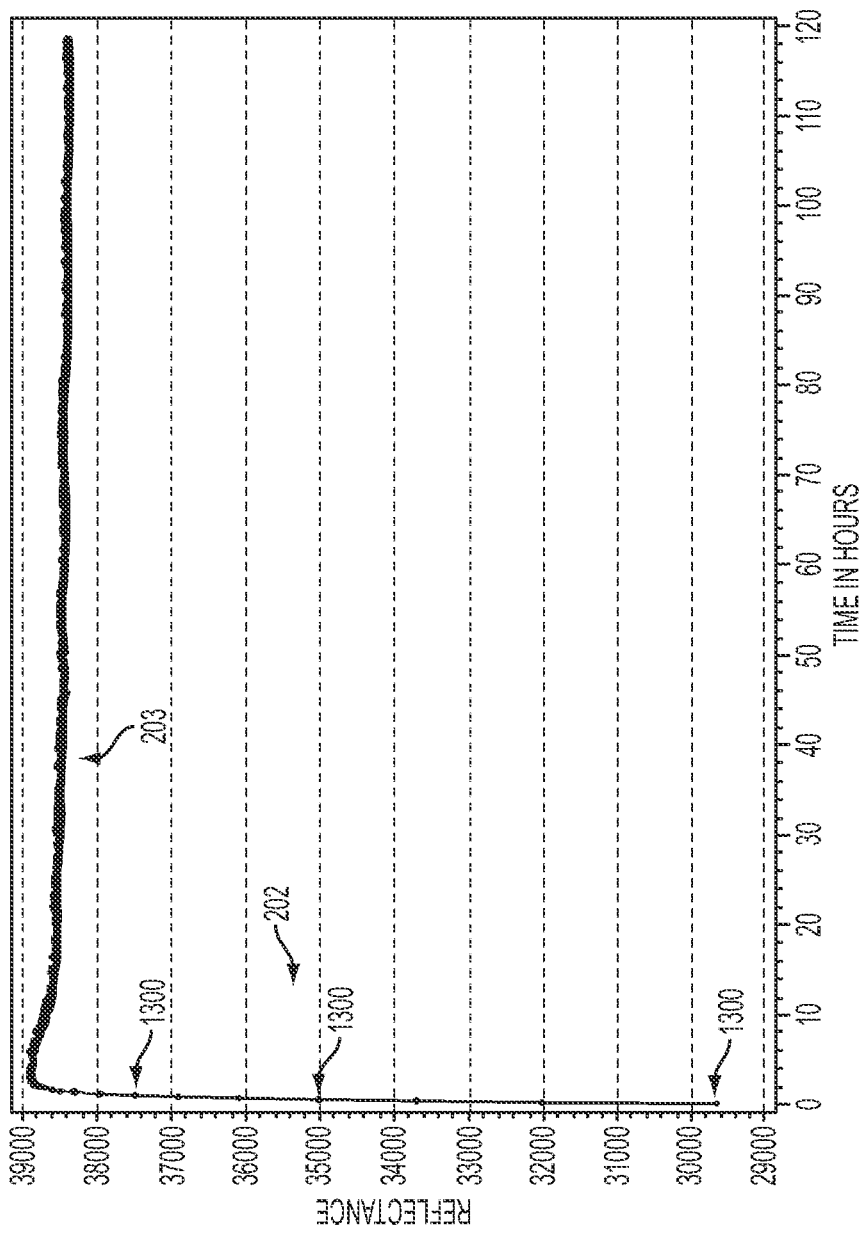
FIG. 13 is an illustration of a plot of microbial growth as a function of time under the "early incubation" scenario in which the container is delayed in being loaded into the detection system for testing; in this scenario the lag phase and most or all of the exponential growth phases of the typical growth curve are absent. One of the methodologies of this disclosure identifies a positive bottle under this scenario. This methodology can be performed in parallel with the point to point variation and relative area under the curve methods described in conjunction with FIGS. 7 and 10.

The growth curve of FIG. 13 is representative of one can be expected in the "delayed entry" situation. The growth curve in this example is plotted as a series of measurements 1300 of intensity or reflectance as a function of incubation time with t=0 being the time that the container is first interrogated by the detection apparatus (see FIG. 1 for example) in the detection instrument. The growth curve includes some part of the exponential growth phase 202 (typically only a small part of the exponential growth phase occurring at the end thereof) and an extended stationary phase 203 typically lasting much longer than the exponential growth phase.

The Early Incubation Methodology provides a separate analysis of the data designed specifically for delayed entry testing. Three different alternative methods can be used in early incubation detection methodology to identify a container as being positive for microbial growth, including a first method calculating a mean reflectance values and comparing to a threshold (see FIG. 14), a second method using mean point-to-point value and comparison to a threshold (see FIG. 15), and a third method in which the number of consecutively increasing point-to-point values are counted and compared to a specified threshold value (see FIG. 16). These methods will be described below.

For this analysis, the following set of input parameters is required.

1. Curve Interval: Number of consecutive reflectance values (1300 in FIG. 13) over which to perform calculations. (Integer)

2. Curve Stabilization Period: Initial period of incubation, in hours, when the reflectance data are considered to be unstable. (Real number)

3. Early Incubation Maximum Time: The maximum incubation time, in hours, to interpret a curve as positive during early incubation. (Real number)

4. Consecutive Increasing Point-to-Point Values Positive Threshold: Threshold value for determining whether a curve is positive when the incubation time is less than the value of Early Incubation Maximum. In general, the number of consecutive increasing point-to-point values must be greater than specified criteria required for a growth curve to be interpreted as positive. (Integer)

5. Mean Point-to-Point Value Positive Threshold: Threshold value for determining whether a curve is positive when the incubation time is less than the value of Early Incubation Maximum. A trimmed mean based on consecutive point-to-point values is calculated and compared to the specified threshold value. The number of consecutive values corresponds to the value of Curve Interval. (Real number)

6. Reflectance Value Positive Threshold: Threshold value for determining whether a curve is positive when the incubation time is less than the value of Early Incubation Maximum. A trimmed mean based on consecutive reflectance values is calculated and compared to the specified threshold value. The number of consecutive values corresponds to the value of Curve Interval. (Integer)

7. Initial Point-to-Point Variation Screen: An upper bound on the point-to-point variation values based on the distribution of values from negative bottles. (Real number)

In general, data available between the end of the Curve Stabilization Period and the Early Incubation Maximum Time are processed using the Early Incubation Methodology. As noted above, there are three alternative ways that a curve can be interpreted as positive using the Early Incubation Algorithm—1) mean reflectance value positive, 2) mean point-to-point value positive, and 3) number of consecutive increasing point-to-point values equal to a specified value. The early incubation methodology can use 1, 2 or all 3 of these methods, for example it can use all three methods in parallel and if any one results in a positive identification the containers is flagged as positive.

Figure 14:
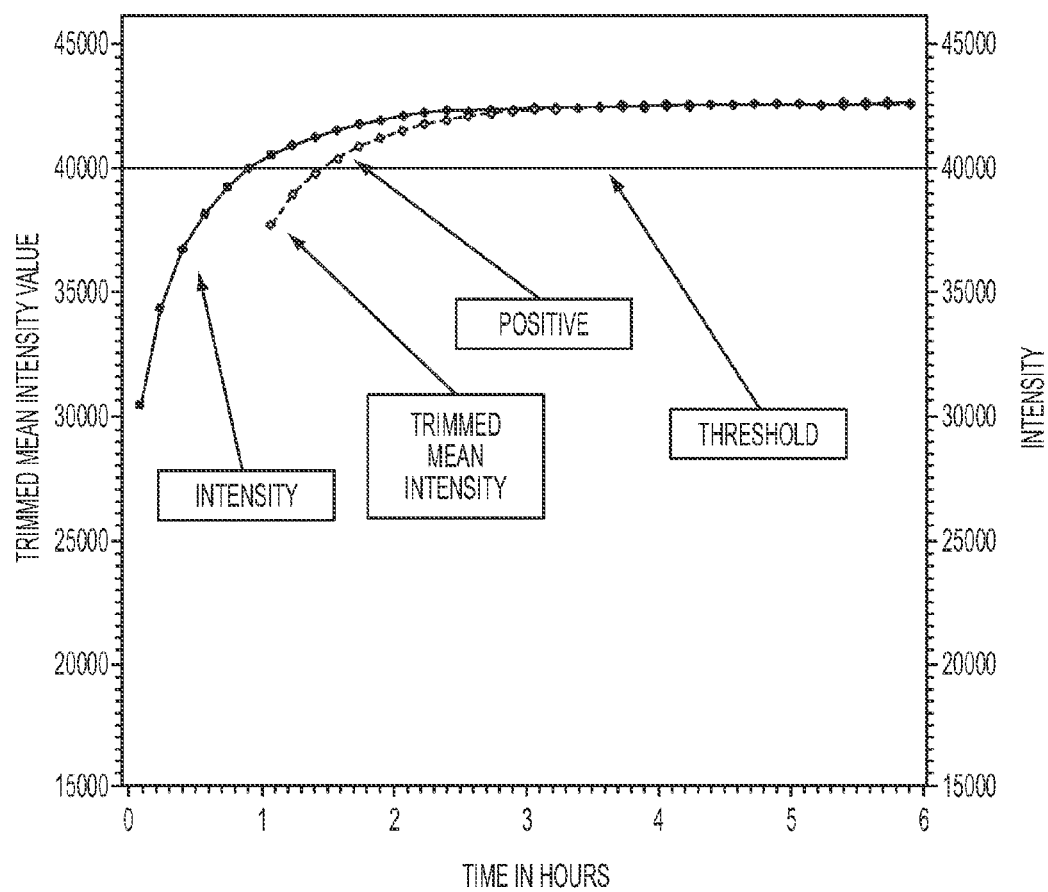
FIG. 14 is an illustration of a mean intensity value positive method for the "late entry" scenario.

1) Mean Reflectance Value Positive Method (See FIG. 14)

The mean reflectance value positive method addresses the case when the lag and most, if not all, of the exponential phase 202 of the reflectance curve is missing, as shown for example in FIGS. 13 and 14. In other words, the curve is mostly just the stationary phase (203 in FIG. 13). The mean reflectance value positive method calculates a trimmed mean of the x most recent reflectance values (1300 in FIG. 13), where x is equal to the value of Curve Interval parameter (as defined above). See FIG. 14. If the currently observed trimmed mean reflectance value is greater than the Reflectance Value Positive Threshold, the growth curve is considered positive and the specimen container is flagged as positive.

The formula for the trimmed mean reflectance value is given by—

Mean Reflectance=[Sum of(Reflectance values 1 to $x$)−Maximum of(Reflectance values 1 to $x$)−Minimum of(Reflectance values 1 to $x$)]/(Curve Interval−2)

where x is defined as the value of Curve Interval.

Figure 15:
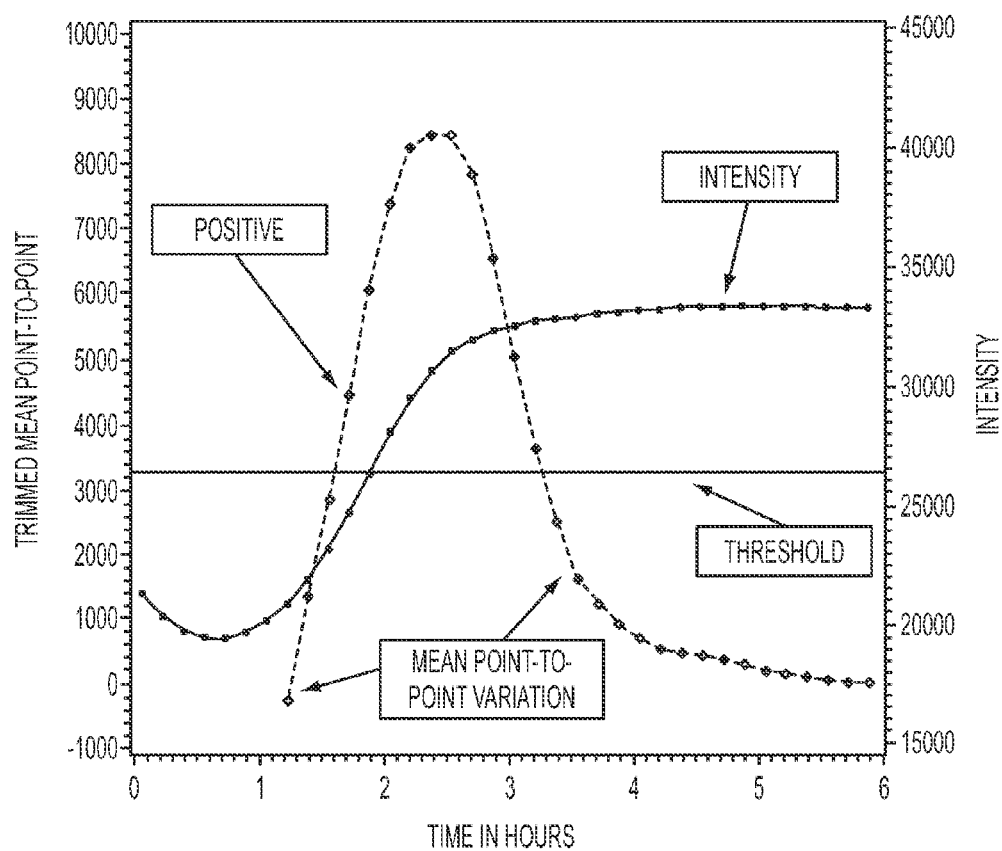
FIG. 15 is an illustration of a mean point-to-point value positive method for the "late entry" scenario.

2) Mean Point-to-Point Value Positive Method (FIG. 15)

The mean point-to-point value positive method is best suited for the case when a sufficient portion of the exponential phase is available for analysis. The plot of FIG. 13 is an example. For this method, the trimmed mean of the x most recent point-to-point values (1300 in FIG. 13) is calculated and compared to the Mean Point-to-Point Value Positive Threshold. If the mean value is greater than the Mean Point-to-Point Value Positive Threshold, the curve is classified as positive. In the example of FIG. 15, the positive classification is made at 1.75 hours, as indicated by the "positive" legend in the Figure.

The formula for the trimmed mean point-to-point (P2P) value is given by—

Mean $P2P$=[Sum of($P2P$ values 1 to $x$)−Maximum of($P2P$ values 1 to $x$)−Minimum of($P2P$ values 1 to $x$)]/(Curve Interval−2)

where x is defined as the value of Curve Interval.

Figure 16:
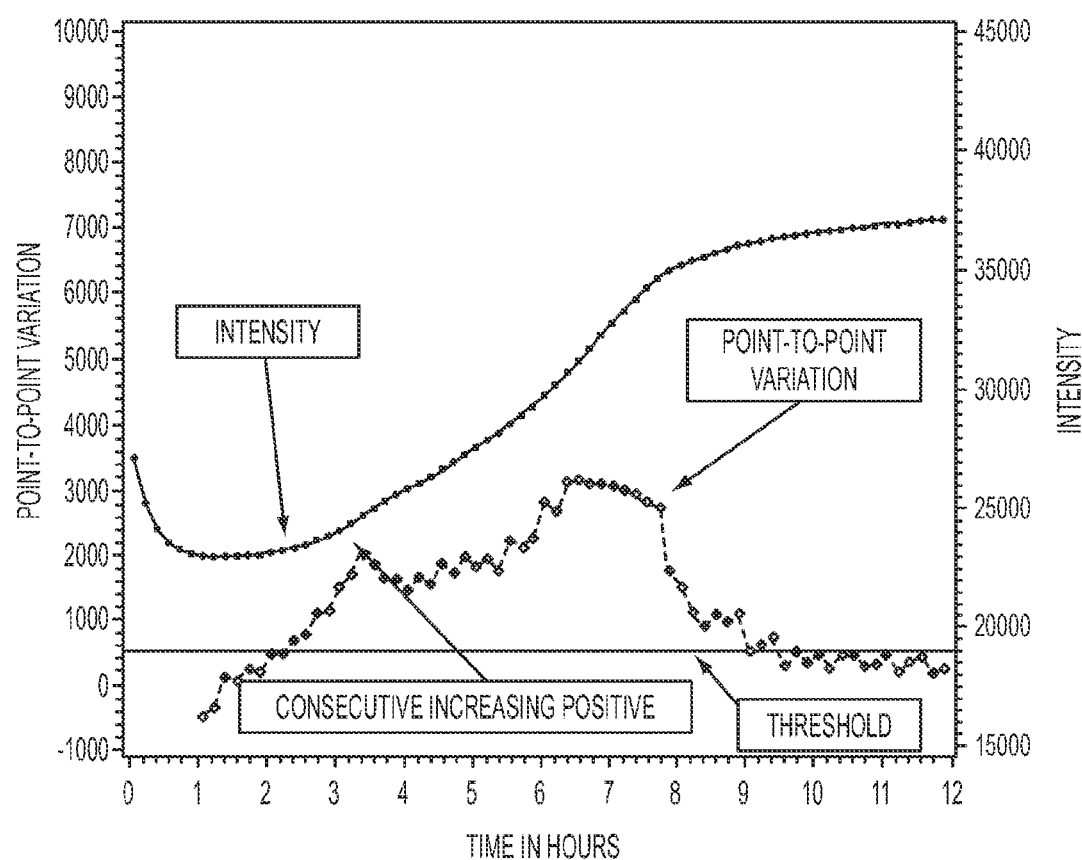
FIG. 16 is an illustration of the number of consecutive increasing point-to-point values greater than a specified value method for the "late entry" scenario.

3) Number of Consecutive Increasing Point-to-Point Values Equal to a Specified Value Method. (FIG. 16)

The number of consecutive increasing point-to-point values greater than a specified value method is also targeted toward cases when a segment of the exponential phase of the reflectance curve is captured, as in the case of FIG. 13. With this approach, each point-to-point value is compared to the Initial Point-to-Point Variation Screen value. If the early incubation point-to-point values are consistently greater than the screen value, it is likely that the reflectance data correspond to the exponential portion of the curve. A counter is used to determine when a sufficient number of consecutive increasing P2P values has been obtained. The counter is computed using the following logic:

If the current P2P value is greater than the value of the Initial Point-to-Point Variation Screen and the current P2P value is greater than 85% of the previous P2P value, increase the counter by 1. Otherwise reset the counter to zero.

Over the early incubation period, the counter is compared to the Consecutive Increasing Point-to-Point Values Positive Threshold. When the counter equals the threshold value, the curve is classified as positive. In the example of FIG. 16, the curve is classified as positive at approximately 2.4 hours, when the consecutive increasing positive plot first crosses the threshold shown in the Figure.

Effect of Input Parameters on Test Interpretation

A set of 5,218 test curves was evaluated using three different combinations of input parameters with the instant method. For comparison purposes, the same 5,218 curves were evaluated using a currently used method in the BacT/ALERT instrument (prior art method). Of the 5,218 test curves, 1,559 do not show evidence of organism growth. The remaining 3,659 curves do exhibit evidence of organism growth. Table 1 summarizes the 3 sets of input parameters. Table 2 provides a comparison of the test results from the instant method with each of the 3 sets of input parameters and the previous method.

TABLE 1

Input Parameter Combinations Evaluated

| Parameter | Set 1 | Set 2 | Set 3 |
| --- | --- | --- | --- |
| Point-to-Point Multiplication Factor | 2 | 1.75 | 1.75 |
| RAUC Multiplication Factor | 19 | 19 | 21 |

TABLE 2

Comparison of Algorithm Results

| | | Instant method | | |
| --- | --- | --- | --- | --- |
| Results | Prior art | Set 1 | Set 2 | Set 3 |
| Correct Negative Interpretation | 1558/1559 99.9% | 1549/1559 99.4% | 1556/1559 99.8% | 1557/1559 99.9% |
| Correct Positive Interpretation | 3622/3659 99.0% | 3659/3659 100.0% | 3649/3659 99.7% | 3646/3659 99.6% |

In addition to test interpretation, the time to detection (TTD) was compared between the methods of this disclosure and a prior art method. Table 3 provides a summary of the comparison.

TABLE 3

Comparison of Time-to-Detection Relative to Prior Art

| Measure | Set 1 | Set 2 | Set 3 |
| --- | --- | --- | --- |
| Mean TTD Reduction In Hours | 2.5 hrs. | 2.2 hrs. | 2.1 hrs. |

Thus, the present inventive methods reduced the time to positive detection of microbial growth by over two hours in each of the three sets as compared to existing methods.

Exemplary Detection Machines/Systems

The methods of this disclosure can be implemented in systems combining incubation, measurement, and processing units, for example the system of Robinson et al., U.S. 2011/0124028 the content of which is incorporated by reference herein, the BacT/ALERT system of the assignee bioMerieux, Inc., competitive systems or systems described in the background patent literature cited above. Such a system is configured an apparatus for incubating the specimen container (e.g., enclosure with supply of warm air), a measurement system (see FIG. 1 or similar arrangement) obtaining a series of measurement data points while the specimen container is incubated and storing the data points in a machine-readable memory, the series of measurement data points representing a growth curve of microbial growth within the specimen container; and a programmed computer performing in parallel analytical methods (a) and (b), namely:

(a) an analysis of variation in successive data points in the series of measurement data points (see e.g., FIGS. 3, 4 and 9A-9B), and (b) an analysis of changes in the area under the growth curve between sets of data points in the series of measurement data points (see e.g., FIGS. 7 and 10A-10B), wherein both analytical methods (a) and (b) include a processing step for determining a positive condition of microbial growth within the container from the measurement data points.

In one embodiment the invention can take the form of a programmed machine readable memory with processing instructions (software) for execution by a general purpose computer for execution of the steps of the method. As one example, the software can take the form of machine-readable code resident on a hard disk or other memory device executing the steps of FIGS. 9-10. As another example, the software can be loaded onto a hard disk and copied to memory within a microbiological testing instrument having specimen container reading apparatus such as shown in FIG. 1 or a similar arrangement.

Figure 17:
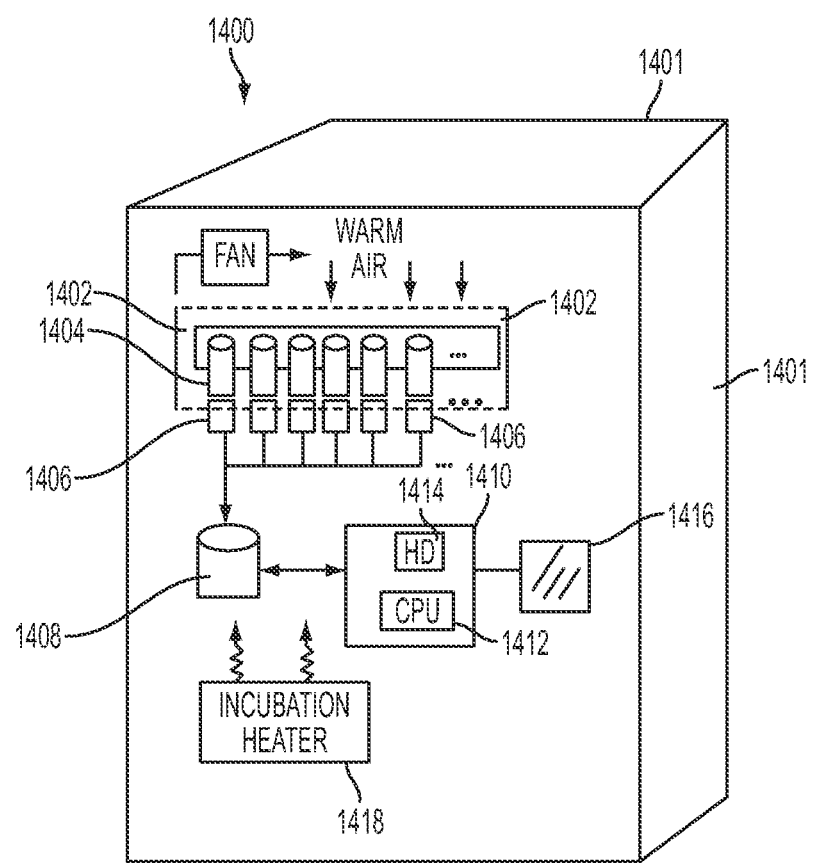
FIG. 17 is a schematic illustration of a detection instrument for detecting containers such as bottles which are positive for microbial growth. The inventive methods of this disclosure are suitable for implementation in a system such as shown in FIG. 17 or equivalent systems.

FIG. 17 is an illustration of a system 1400 in the form of a machine for detecting containers (such as bottles) for positive microbial growth. The system includes insulated walls 1401 and an incubation heater 1418 (conventional) supplying warm air to the interior defined by the walls in order to incubate the containers stored therein in a controlled environment such as 30 degrees C. The system 1400 includes an access door or drawer 1402 which provides access to holders 1404 for the containers, such as for example holders with a bottle form factor for receiving blood culture bottles or the like.

The system 1400 is configured with multiple measurement units 1406 which may for example take the form of a light source and detector shown in FIG. 1 and described previously. The measurement units 1406 measure reflectance from the containers and supply reflectance measurements (data points) in digital form to a computer-readable memory 1408. The system further includes a general purpose computer 1410 having a central processing unit 1412 and a hard disk memory 1414 storing program code for analyzing the measurements data pair (reflectance value, time). The program code implements the analytical methods described in detail above, namely the point-to-point variation method, the relative area under the curve method and the methods for "late entry" determination of positive containers described in conjunction with FIGS. 13-16. The system 1400 further includes a display 1416 coupled to the computer 1410 which displays messages to the operator, for example the status of the containers incubated in the system 1400 and whether and when some container has been detected positive.

It will be appreciated that the system shown in FIG. 17 will typically have other features for processing and handling specimen containers, agitating containers, etc. as customary in machines of this sort which are commercially available and described in the art. These details are omitted from the present discussion since they are not particularly relevant. The interested reader is directed to Bac-T/ALERT 3D instrument of the assignee as well as Robinson et al., U.S. patent application publication no. 2010/0291619 as an example of such a system. The description of the detection system in the '619 is incorporated by reference as an example of a system in which the inventive methods can be implemented. It will also be appreciated that all of the above descriptions as to the operation of the inventive methods will be applicable to the system shown in FIG. 17.

Thus, for example, in one aspect a system (1400) for determining whether microbial growth is occurring within a specimen container (e.g., bottle of FIG. 1) is disclosed which includes apparatus (1401, 1418) for incubating the specimen container; a measurement system (1406, FIG. 1) obtaining a series of measurement data points from the specimen container while the specimen container is incubated and storing the data points in a machine-readable memory (1408), the series of measurement data points representing a growth curve of microbial growth within the specimen container; and a programmed computer (1410, CPU 1412) performing in parallel analytical methods (a) and (b), namely:

(a) an analysis of variation in successive data points in the series of measurement data points (described above in conjunction with FIGS. 3, 4, 9A-9B), and (b) an analysis of changes in the area under the growth curve between sets of data points in the series of measurement data points (described above in conjunction with FIGS. 7 and 10A-10B), wherein both analytical methods (a) and (b) include a processing step for determining a positive condition of microbial growth within the container from the measurement data points.

As another example, a microbiological testing machine (1400) is disclosed which comprises an incubation system (1418) for incubating a plurality of specimen containers, a measurement system (1406, FIG. 1) obtaining a series of measurement data points from the specimen containers while the incubation system incubates the specimen containers, a machine-readable memory (1408) storing the measurement data points, the series of measurement data points representing a growth curve of microbial growth within the specimen container; and a processing unit 1412 operative to determine whether the containers are positive for microbial growth, the processing unit 1412 executing a sequence of program instructions analyzing the series of measurement data points, wherein the container was delayed in obtaining the measurement data points such that a lag phase and most or all of an exponential growth phase in the growth curve are not present.

While presently preferred embodiments have been described, it will be appreciated that variation from the specifics of the disclosed embodiments is possible without departure from the scope of the invention. All questions concerning scope are to be answered by reference the appended claims.

The invention claimed is:

1. A method for determining whether microbial growth is occurring within a specimen container comprising the steps of:
   incubating the specimen container comprising a sample medium and a growth medium;
   obtaining a series of measurement data points from the specimen container while the specimen container is incubated and storing the data points in a machine-readable memory, the series of measurement data points representing a growth curve of microbial growth within the specimen container from the sample medium;
   performing with a programmed computer, a process comprising in parallel analytical methods (a) and (b), namely:
   (a) performing an analysis of variation in successive data points in the series of measurement data points, and
   (b) performing an analysis of changes in the area under the growth curve between sets of data points in the series of measurement data points;
   defining an interval of time during which analytical method (b) is prevented from making a determination of a positive condition in the specimen container when a difference between a current test value and a previous test value is greater than an upper threshold or less than a lower threshold, wherein the upper threshold and the lower threshold are based on the analysis of variation in successive data points in analytical method (a);
   determining a positive condition of microbial growth within the container from the measurement data points based on at least one of analytical methods (a) and (b); and
   ending the incubation when at least one of analytical methods (a) and (b) determines that the positive condition is present in the specimen container, or the process reaches a maximum incubation time.

2. The method of claim 1, further comprising determining instances of measurement error in the series of measurement data points in analytical method (a).

3. The method of claim 1, further comprising calculating real time decision thresholds for a positive interpretation of microbial growth using the measurement data points in both analytical methods (a) and (b).

4. The method of claim 1, further comprising performing analytical method (c) in parallel with analytical methods (a) and (b), analytical method (c) comprising an analysis of the series of measurement data points under a scenario in which the container was delayed in obtaining the measurement data points such that a lag phase in a growth curve associated with the measurement data points are not present.

5. The method of claim 4, wherein the analytical method (c) comprises at least one of the following methods: a first method calculating a mean measurement data point value and comparing such mean measurement data point value to a threshold, a second method calculating a mean measurement data point-to-point value and comparing such mean to a threshold, and a third method in which a number of consecutively increasing measurement data point-to-point values are counted and compared to a specified threshold value.

6. The method of claim 5, wherein analytical method (c) comprises performing the first, second and third methods in parallel.

7. The method of claim 1, wherein the specimen container comprises a bottle.

8. The method of claim 7, wherein the bottle includes an internal colorimetric sensor.

9. The method of claim 7, wherein the specimen container contains a biological sample obtained from a human.

10. The method of claim 9, wherein the biological sample comprises blood or a blood product.

* * * * *